(12) United States Patent
Hidaka et al.

(10) Patent No.: US 8,157,539 B2
(45) Date of Patent: Apr. 17, 2012

(54) ARTIFICIAL HEART PUMP

(75) Inventors: Tatsuya Hidaka, Takasago (JP);
Toshiyuki Osada, Takasago (JP);
Takeshi Okubo, Takasago (JP); Yohei Kakiuchi, Takasago (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 622 days.

(21) Appl. No.: 11/991,415

(22) PCT Filed: Sep. 7, 2006

(86) PCT No.: PCT/JP2006/317732
§ 371 (c)(1),
(2), (4) Date: Mar. 4, 2008

(87) PCT Pub. No.: WO2007/032249
PCT Pub. Date: Mar. 22, 2007

(65) Prior Publication Data
US 2009/0259308 A1    Oct. 15, 2009

(30) Foreign Application Priority Data
Sep. 13, 2005    (JP) ................................ P2005-265664

(51) Int. Cl.
*F04B 35/04*    (2006.01)
*A61M 1/10*    (2006.01)
*A61M 37/00*    (2006.01)
*F01D 3/00*    (2006.01)

(52) U.S. Cl. ............... 417/353; 417/423.12; 600/16; 623/3.14; 415/104; 415/107; 604/6.11

(58) Field of Classification Search ................ 417/352, 417/353, 355, 356, 413.2, 423.13; 623/3.1–3.26; 600/16, 17; 415/104, 107, 900; 604/6.11; 310/90.5, 86
See application file for complete search history.

(56) References Cited

U.S. PATENT DOCUMENTS

| | | | | |
|---|---|---|---|---|
| 2,898,032 A * | 8/1959 | Katzenberger | ............... | 417/244 |
| 3,938,913 A * | 2/1976 | Isenberg et al. | ............... | 417/356 |
| 4,625,712 A | 12/1986 | Wampler | | |
| 5,112,200 A * | 5/1992 | Isaacson et al. | ............... | 417/356 |
| 5,211,546 A * | 5/1993 | Isaacson et al. | ............... | 417/356 |
| 5,219,276 A * | 6/1993 | Metzner et al. | ............... | 417/356 |
| 5,494,413 A | 2/1996 | Campen et al. | | |
| 5,527,159 A * | 6/1996 | Bozeman et al. | ............... | 417/45 |
| 6,015,272 A * | 1/2000 | Antaki et al. | ............... | 417/356 |
| 6,053,705 A | 4/2000 | Schob et al. | | |
| 6,139,267 A * | 10/2000 | Sedlacek et al. | ............ | 415/219.1 |

(Continued)

FOREIGN PATENT DOCUMENTS

JP    61-600069 A    1/1986

(Continued)

*Primary Examiner* — Devon C Kramer
*Assistant Examiner* — Bryan Lettman
(74) *Attorney, Agent, or Firm* — Birch, Stewart, Kolasch & Birch, LLP

(57) ABSTRACT

By inserting a protruding portion (8*b*), which is installed to a center position of a rear end surface (8*x*) of a fixed body (8), into a hole (4*a*), which is provided to a center position of an end surface (4*x*) on a side of a fixed body (8) of a fixed shaft (4) that is connected to a fixed body (3), the fixed bodies (3) and (8) and the fixed shaft (4) are connected. As a result, a sleeve (5) can be removed only by dismantling the fixed body (3).

28 Claims, 25 Drawing Sheets

U.S. PATENT DOCUMENTS

| | | | |
|---|---|---|---|
| 6,186,665 B1 * | 2/2001 | Maher et al. | 384/206 |
| 6,368,075 B1 * | 4/2002 | Fremerey | 417/365 |
| 6,447,265 B1 * | 9/2002 | Antaki et al. | 417/354 |
| 6,581,476 B1 * | 6/2003 | Fremerey | 73/861.77 |
| 6,742,999 B1 | 6/2004 | Nusser et al. | |
| 7,502,648 B2 | 3/2009 | Okubo et al. | |
| 2004/0241019 A1 * | 12/2004 | Goldowsky | 417/423.1 |

FOREIGN PATENT DOCUMENTS

| | | | |
|---|---|---|---|
| JP | 63-285329 A | 11/1988 | |
| JP | 7-189972 A | 7/1995 | |
| JP | 7-305697 A | 11/1995 | |
| JP | 8-504490 A | 5/1996 | |
| JP | 10-179729 A | 7/1998 | |
| JP | 2000-502420 A | 2/2000 | |
| JP | 2001-12456 A | 1/2001 | |
| JP | 2001-500569 A | 1/2001 | |
| JP | 2001-123978 A | 5/2001 | |
| JP | 2001-514532 A | 9/2001 | |
| JP | 2003-501155 A | 1/2003 | |
| JP | 2003-503639 A | 1/2003 | |
| JP | 2003-174742 A | 7/2003 | |
| JP | 2003-525069 A | 8/2003 | |
| JP | 2004-329236 A | 11/2004 | |
| JP | 2004-346930 A | 12/2004 | |
| JP | 2004-351213 A | 12/2004 | |
| JP | 2005-118237 A | 5/2005 | |
| JP | 2007-75287 A | 3/2007 | |
| WO | WO 85/01432 A1 | 4/1985 | |
| WO | WO-94/09274 A1 | 4/1994 | |
| WO | WO 97/49440 A2 | 12/1997 | |
| WO | WO 98/11347 A1 | 3/1998 | |
| WO | 00/74748 A1 | 12/2000 | |
| WO | WO0102724 | * | 1/2001 |
| WO | WO2004096320 | * | 4/2004 |

* cited by examiner

ARTIFICIAL HEART PUMP

TECHNICAL FIELD

The present invention relates to an artificial heart pump and especially relates to an artificial heart pump employing an axial-flow pump that pumps the blood.

BACKGROUND ART

Conventionally, an artificial heart pump which pumps the blood by utilizing the rotation of the impeller is employed as an alternate being used for medical purposes or as an assist pump being used for medical purposes. An artificial heart pump utilizing a roller pump or a centrifugal pump and an artificial heart pump utilizing an axial-flow pump are provided as the aforementioned artificial heart pump. Among these various types of artificial heart pumps, the artificial heart pump utilizing an axial-flow pump can reduce the size thereof, being compared with the artificial heart pump utilizing a roller pump or a centrifugal pump.

The conventional artificial heart pump utilizing an axial-flow pump includes a housing that houses motor stators therein, and at the same time, includes a rotor being equipped with impellors on the circumference thereof that houses permanent magnets reacting to the motor stators magnetically therein. As an artificial heart pump that has been described hereinabove, as shown in FIG. 24, a following artificial heart pump is provided: wherein, a rotor 104 being equipped with impeller vanes 105 on the outer circumference thereof is installed between fixed bodies 102 and 103 that are fixed to a housing 101; and pivot bearings 106a and 106b are installed to the surfaces where the fixed bodies 102 and 103 face toward the rotor 104. To be specific, by having the centers of the surfaces of the rotor 104 facing the fixed bodies 102 and 103 stick out, the pivot bearings 106a and 106b are formed.

However, when the rotor is supported by the pivot bearings 106a and 106b as shown in FIG. 24, abrasion powders are sometimes generated in the pivot bearings 106a and 106b. In addition, because the gap between the fixed body 102 and the rotor 104 and the gap between the fixed body 103 and the rotor 104 become narrow, there is a possibility that a blood clot may be formed easily or that red blood cells may be destructed.

On the other hand, as shown in FIG. 25, a following artificial heart pump is provided: wherein, the fixed bodies 102 and 103 are connected by the fixed shaft 121; and a rotor 122 having a cylindrical shape, and rotating along the outer circumference of the fixed shaft 121 is installed; and at the same time, hydrodynamic bearings are constructed by providing a groove to each of the surfaces where the rotor 122 faces the fixed bodies 102 ad 103, respectively. To be specific, by having the rotor 122 rotate, hydrodynamic pressures are generated in the grooves that are provided to the surfaces of the fixed bodies 102 and 103 facing the rotor 122, respectively, and thereby, the rotor 122 is prevented from contacting the fixed bodies 102 and 103, and the dynamic bearings behave as thrust bearings. However, when such hydrodynamic bearings are configured as mentioned above, narrow gaps will be necessary for generating the hydrodynamic pressures, and as a result, due to the narrow gaps, there is a possibility that a blood clot may be formed easily or that red blood cells may possibly be destructed.

In order to prevent the above-mentioned problems, the present applicant proposes an artificial heart pump that prevents the rotor from contacting the fixed bodies by passive type of repulsive magnetic bearings, which not only construct the hydrodynamic bearings but also utilize the magnetic forces of repulsion balancing the hydro thrust loads being applied on the impeller vanes. (See the Patent Reference No. 1.) As shown in FIG. 26, in addition to the configuration shown in FIG. 25, the artificial heart pump that is equipped with the passive type of repulsive magnetic bearings has permanent magnets 131 and 132 installed to each of the rotor 122 and the fixed body 103, whereby the passive type of repulsive magnetic bearings are constructed by the magnetic forces of repulsion that balance the hydro thrust loads.

Patent Reference 1: Japanese Patent Application, First Publication No. 2004-346930

DISCLOSURE OF THE INVENTION

Issues to Be Solved by the Present Invention

However, in a case of artificial heart pumps having such configuration as shown in the aforementioned FIG. 25 and FIG. 26, respectively, fixed bodies 102 and 103 that are connected by a fixed shaft 121 are fixed to a housing 101 by way of a stationary vane and a diffuser vane, respectively. Therefore, in a case where only the rotor 122 is dismantled for an internal inspection and the like, it is necessary to disassemble all fixed members including the fixed bodies 102 and 103 and the fixed shaft 121. In addition, not only an assembly performance is inferior, but also it is difficult to adjust the face-to face distance between the bearing, which is formed by the axial fixed body 102 and the rotor 122, and the face-to face distance between the bearing, which is formed by the axial fixed body 103 and the rotor 122, when the repulsive magnetic bearings are provided as shown in FIG. 26.

Moreover, in a case of the artificial heart pumps shown in FIG. 25 and FIG. 26, respectively, the motor stator that is housed in a housing 101 and the permanent magnets that are housed in the rotor 122 not only rotate the rotor 122 but also function to serve as journal bearings that prevent a radial contact of the rotor 122 with the fixed shaft 121. However, since the permanent magnets are provided to the inside diameter of the rotor 122, the outside diameter of the rotor 122 being equipped with the impeller vanes becomes large. In addition, when high pressures are necessary, it is required to increase the rotation speed of the rotor 122. However, when the rotation speed is increased and becomes high, the characteristic of destruction of red blood cells will be worsened. Therefore, the size of the artificial heart pump is limited, whereby the upper limit of the pressure thereof will be limited.

Furthermore, when the hydrodynamic bearings are configured as shown in FIG. 25, narrow gaps will be necessary for generating the hydrodynamic pressures, and as a result, due to the narrow gaps, there is a possibility that a blood clot may be formed easily or that red blood cells may possibly be destructed. On the other hand, in a case of an artificial heart pump that is equipped with such a passive type of repulsive magnetic bearing as shown in FIG. 26, the gap can be made wider than an artificial heart pump that is equipped only with the hydrodynamic bearings as shown in FIG. 25. Therefore, the generation of a blood clot and the destruction of red blood cells can be reduced. However, a contact is caused between the rotor and the fixed member at the back of the rotor due to a magnetic force of repulsion during an operation under a condition that the hydro thrust load is small and during start-ups and shutdowns. In addition, depending on the operation condition, there is a possibility that a contact may be caused between the rotor and the fixed members that are in front of and at the back of the rotor. With such a configuration as shown in FIG. 25, only the convex portion of a hydrodynamic bearing gap is in contact, but the contact area thereof is relatively large, so that there is a problem with a durability thereof. Moreover, by such a configuration as described hereinabove, there are possibilities that abrasion powders may be generated due to the contact of the rotor with the fixed bodies and that a blood clot and a destruction of red blood cells may occur.

Additionally, a conventional artificial heart pump consists of a stator coil that is provided with a slot for winding a coil, in order to obtain a large torque, and serves as a motor stator that is housed in a housing. However, in a case of a stator coil that is provided with a slot, the outside diameter of the housing becomes large for the amount of the slot breadth, whereby downsizing of the artificial heart pump is prevented. Furthermore, in the artificial heart pumps shown in FIG. 25 and FIG. 26, respectively, because permanent magnets are housed in the rotor 122 and configured as synchronous motors, loss of synchronism easily occurs due to a fluctuation in the load, and there is a risk that the artificial heart pump may stop.

Means to Solve the Issue

It is an object of the present invention to provide an artificial heart pump that is configured in a manner that a part of the fixed bodies is independent and can be disassembled. It is another object of the present invention to provide an artificial heart pump that can be downsized axially or radially. In addition, it is another object to provide an artificial heart pump that can increase the discharge pressure without increasing the rotation speed. Moreover, it is another object to provide an artificial heart pump that can prevent a loss of synchronism due to a fluctuation in the load from occurring.

In order to achieve the above-mentioned object, an artificial heart pump in accordance with the present invention comprises: a housing having an inlet and outlet for blood flow; a fixed shaft that is fixed to a center position inside the housing in a direction from the inlet to the outlet; a first fixed body, which is fixed inside the housing with a plurality of stationary vanes at an inlet side of the housing and connected to a front-end of the fixed shaft; a second fixed body, which is fixed inside the housing with a plurality of diffuser vanes at an outlet side of the housing and connected to a rear-end of the fixed shaft; a rotating body that is engaged to the fixed shaft and rotatably supported by a circumferential surface of the fixed shaft; a plurality of impeller vanes that stick out from an outside wall surface of the rotating body; motor stators, which are placed in the housing, located at positions encircling the rotating body, and generate a rotating magnetic field inside the housing; a first and a second permanent magnet, which are housed inside the rotating body and the first fixed body, respectively, generating repulsing magnetic force working in an opposite direction to thrust loads that are applied from a rear side toward a front side in an axial direction of the impeller vanes when the rotating body rotates; and a protruding portion that is provided to a front-end surface of the second fixed body facing a rear-end surface of the rotating body; wherein, the first and the second fixed bodies are provided with structures for separation to be separated from the fixed shaft; and only one of the first and the second fixed bodies can be separated from fixed bodies using the structure for separation; and blood flows in an axial direction of the fixed shaft, by having the rotating body rotate by a rotating magnetic field of the motor stators during operation.

In addition the artificial heart pump in accordance with the resent invention comprises: a housing having an inlet and outlet for blood flow; a fixed shaft that is fixed to a center position inside the housing in a direction from the inlet to the outlet; a first fixed body that is fixed inside the housing with a plurality of stationary vanes at an inlet side of blood flow; a second fixed body, which is fixed inside the housing with a plurality of diffuser vanes at an outlet side of blood flow and connected to a rear end of the fixed shaft; a rotating body, which is installed between the first and the second fixed bodies, engaged to the fixed shaft, and rotatably supported by a circumferential and front-end surfaces of the fixed shaft; a plurality of impeller vanes that stick out from an outside wall surface of the first rotating body; and motor stators that are placed in the housing, located at positions encircling the rotating body, and generate a rotating magnetic field therein; wherein, the rotating body covers the circumferential and front-end surfaces of the fixing shaft; a bottom portion is formed in the front-end surface of the rotating body; the bottom portion of the rotating body is supported by rear-end surface of the first fixed body without physical contact; a hole allowing blood flow is formed at a center position of the bottom portion of the rotating body; the rotating body and the first fixed body have insides thereof provided with a first and a second permanent magnets, respectively, which generate repulsing magnetic force working in an opposite direction to thrust loads, which are applied from a rear side toward a front side in an axial direction of the impeller vanes, when the rotating body rotates; and blood flows in an axial direction of the fixed shaft, by having the rotating body rotate by a rotating magnetic field of the motor stators during operation.

Moreover, the artificial heart pump in accordance with the present invention comprises: a housing having an inlet and outlet for blood flow; a first fixed body, which is fixed inside the housing with a plurality of stationary vanes at an inlet side of the housing; a second fixed body, which is fixed inside the housing with a plurality of diffuser vanes at an outlet side of the housing; a rotating body that is installed between the first and the second fixed bodies; a plurality of impeller vanes that stick out from an outside wall surface of the rotating body; and motor stators, which are placed in the housing, located at positions encircling the rotating body, and generate a rotating magnetic field therein; and, a rotor, which is placed in the rotating body, rotates the rotating body by generating induced electric currents by a rotating magnetic field of the motor stators; wherein, blood flows in an axial direction by having the rotating body rotate by a rotating magnetic field of the motor stators during operation.

Effects of Invention

In accordance with the present invention, by being provided with a structure for separation of the fixed bodies that can separate the fixed bodies by the fixed shaft, and by being able to remove only one of the first and the second fixed bodies, it is not necessary to dismantle both first and second fixed bodies to be disassembled as in a conventional manner. In addition, during assembly of an artificial heart pump, the assembly quality thereof can be enhanced. Moreover, by using an adjustment ring, or by having the structure for separation of the fixed bodies constructed by a first and a second fixed shafts that are made by splitting the fixed shaft, a distance between the first and the second fixed bodies can be adjusted. As a result, the face-to-face dimension between the bearings can be easily adjusted when a repulsive magnetic bearing is applied to a thrust bearing.

In accordance with the present invention, since the first permanent magnet is installed to the bottom portion of the rotating body, the first permanent magnet can be installed so as to be stacked radically on an anisotropic permanent magnet and a rotor. As a result, it is not necessary to line them up axially, so that the axial length of the artificial hear pump can be shortened, whereby the artificial heart pump can be downsized. In addition, by providing the bottom portion with a through hole, the blood can be prevented from stagnating without interrupting the flow of blood streaming into a gap between the fixed shaft and the rotating body.

In accordance with the present invention, by being provided with a journal bearing that holds the first rotating body in a radial direction thereof between the first and the second fixed bodies and the first rotating body, it is unnecessary to form the first rotating body in a ring and to install the fixed shaft in the center position of the first rotating body, whereby the first rotating body can be formed to have a cylindrical shape. In consequence, it is possible to shift the positions to install the anisotropic magnet and the rotor radially toward the center position, and thereby, the radial size of the rotating body can be reduced, so that the artificial heart pump can be downsized.

In addition, by installing a second rotating body that is different from the first rotating body being equipped with impeller vanes, impeller vanes can be provided to a plurality of rows, so that the discharge pressure can be increased without increasing the rotating speed of the artificial heart pump, and thereby can enhance the hemolytic property of the artificial heart pump.

Moreover, by forming the surfaces of a first and a third permanent magnets, which face toward a second and a fourth permanent magnets, so as to be convex, and by forming the surfaces of the second and the fourth permanent magnets, which face toward the first and the third permanent magnets, so as to be concave, an axial function of the thrust bearing and a radial function of the journal bearing can be made to work simultaneously by each of actions of the first through the fourth permanent magnets.

In accordance with the present invention, by forming a protruding portion either on a surface facing toward the rotating body of the second fixed body or on a surface facing toward the second fixed body of the rotating body, the rotating body and the second fixed body can have contact with each other by the protruding portion when the rotating body and the second fixed body comes to contact during start-ups and shutdowns, so that the contact area can be reduced. In consequence, the amount of abrasion powders being generated by contact and the possibility of occurrence of blood clot and destruction of blood cells can be restrained. Moreover, by providing the bottom portion of the rotating body with a through hole when the protruding portion is installed to the center of the bottom portion of the rotating body, or by installing a plurality of the protruding portions to the second fixed body at intervals, it is possible to prevent the blood from stagnating without interrupting the flow of blood streaming into a gap between the rotating body and the second fixed body.

In accordance with the present invention, by providing the rotating body with a plurality of rows of impeller vanes, the discharge pressure can be increased without raising the rotating speed of the artificial heart pump, and thereby, the hemolytic property of the artificial heart pump can be enhanced. In addition, by making the motor stators include stator coils having no slots, the artificial hear pump can be shortened radially for the amount of the slots when it is compared with an artificial heart pump that includes stator coils having slots. As a result, the artificial heart pump can be downsized. Moreover, by being provided with a rotor that rotates the rotating body by generating the induced electric currents by the rotating magnetic fields of the motor stators, an induced motor can be composed of the motor stators and the rotor, whereby the loss of synchronism due to a fluctuation in the load and the like can be difficult to occur. Furthermore, since the fixed bodies and the rotating body are made of materials that are different in hardness, a seizure at the time of a contact can be prevented, and thereby, the sliding property can be maintained as favorable.

DESCRIPTION OF CODES

1: Housing
2: Diffuser vane
3: Fixed Body
4: Fixed Shaft
5: Sleeve
6: Impeller Vane
7: Stationary vane
8: Fixed Body
9: Adjustment Ring

BEST MODE FOR CARRYING OUT OF THE INVENTION

First Embodiment

Figure 1:
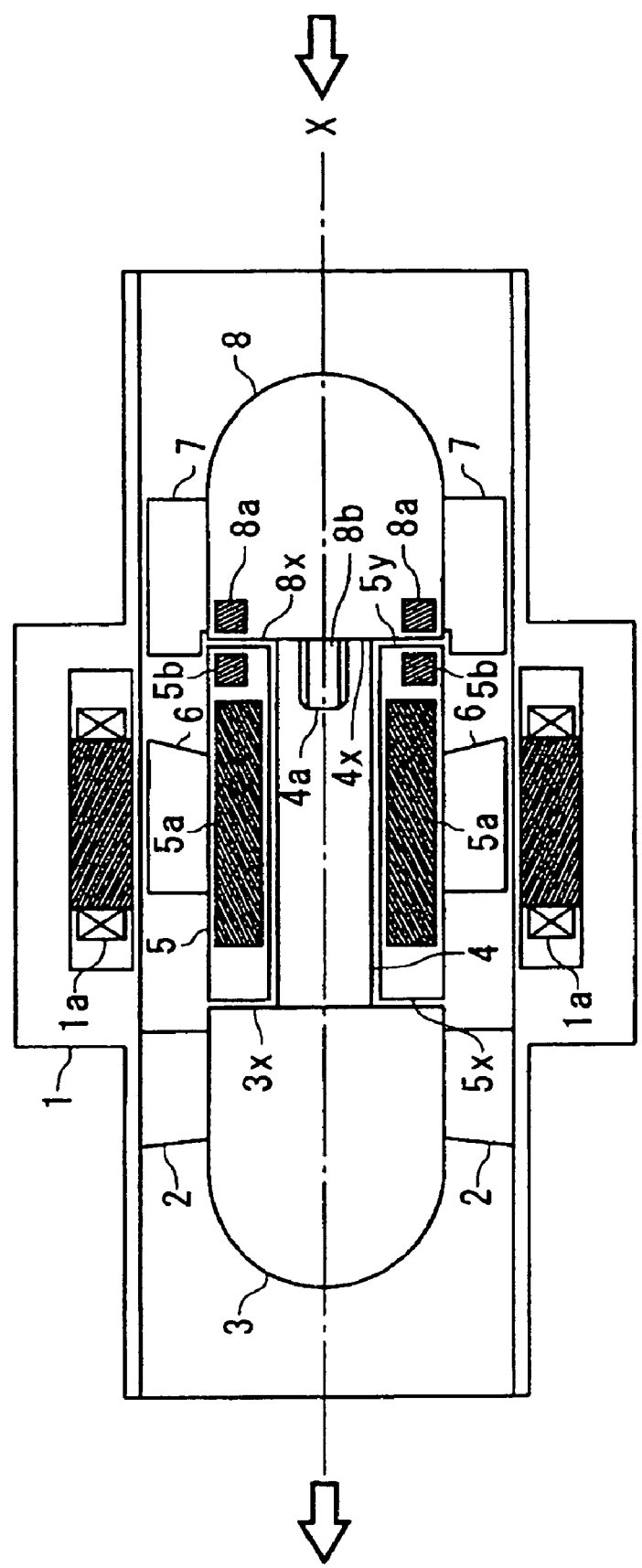
FIG. 1 is a cross-sectional view showing a configuration of an artificial heart pump in accordance with a first embodiment of the prevent invention.
Figure 26:
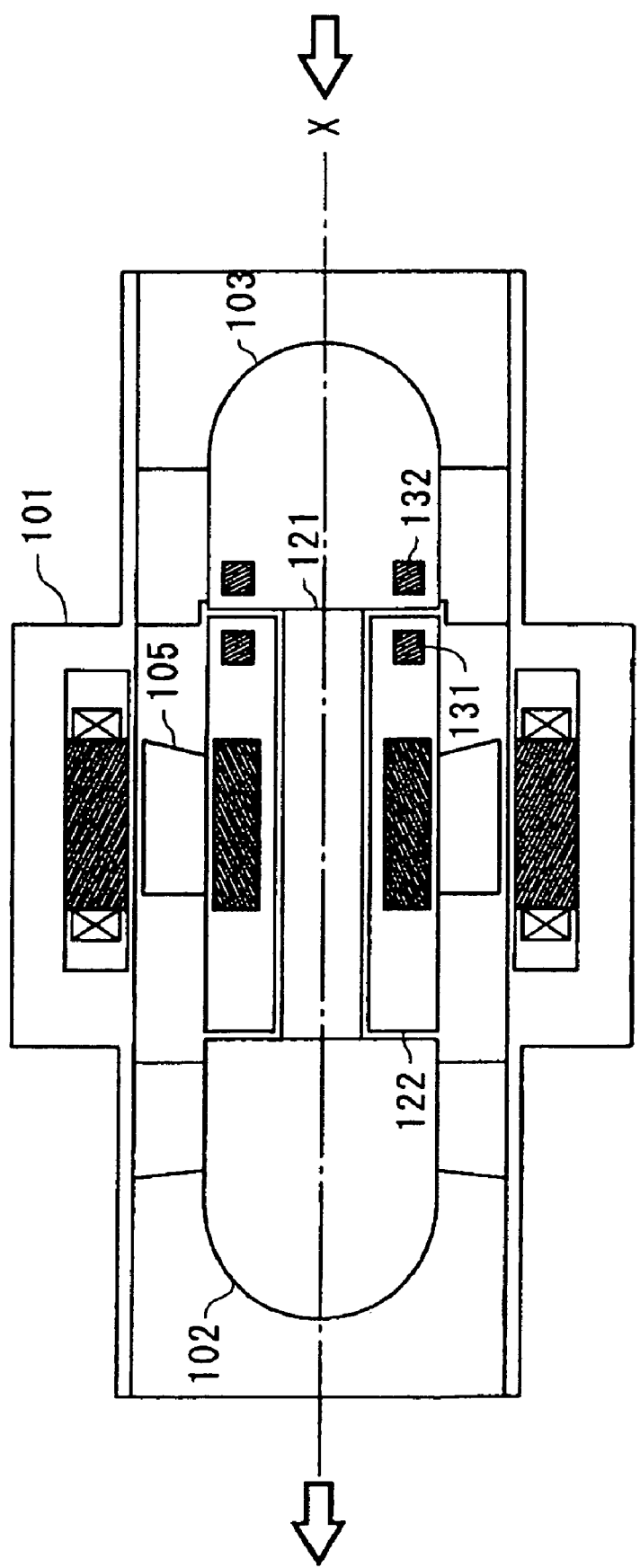
FIG. 26 is a cross-sectional view showing a configuration of a conventional artificial heart pump employing passive type of repulsive magnetic bearings.

Referring now to the drawings, a first embodiment of the present invention will be described hereinafter. FIG. 1 is a cross-sectional view showing a configuration of an artificial heart pump in accordance with the present embodiment. Hereinafter, the words "before/front" and "after/rear" will be referred as the front side (upstream-side) and the rear side (downstream-side) respectively, in accordance with the flow of the blood. In addition, same as FIG. 26, an artificial heart pump in FIG. 1 will be described by taking an artificial heart pump, being provided with both hydrodynamic bearings and passive type of repulsive magnetic bearings, as an example.

An artificial heart pump in FIG. 1 comprises a cylindrical housing 1; a plurality of diffuser vanes 2 that are connected to an inside wall surface of the housing 1; a fixed body 3 that is supported by the housing 1 by having a plurality of diffuser vanes 2 stick out from an outside wall surface thereof a fixed shaft 4 that is installed to a front of the fixed body 3; a sleeve 5 that is installed so as to be around the fixed shaft 4, and rotates around an outer circumference of the fixed shaft 4; a plurality of impeller vanes 6 that stick out from an outside wall surface of the sleeve 5: a plurality of stationary vanes 7 that are installed so as to be located more front-side than the impeller vanes 6; and a fixed body 8 that is connected to the fixed shaft 4 so as to be supported, and has the stationary vanes 7 stick out from the outside wall surface thereof. In addition, outer edges of the stationary vanes 7 and the inside wall surface of the housing 1 are not connected to each other, but have a gap provided therebetween.

The artificial heart pump has the inside of the sleeve 5 provided with polar anisotropic permanent magnets 5a as well as has the inside of the housing 1 provided with motor stators 1a consisting of magnet coils that have magnetic poles thereof face toward the outside wall surface of the sleeve 5. In addition, a plurality of polar anisotropic permanent magnets 5a are provided in a radial pattern with the central axis X of the artificial heart pump serving as the center thereof; wherein, the direction of the magnetic flux thereof is vertical against the inside wall surface of the housing 1. Moreover, the magnetic poles of the adjacent polar anisotropic permanent magnets 5a that face toward the inside wall surface of the housing 1 are made to have a reverse polarity. Consequently, by having electric currents of different phase, such as three-phase electric currents and the like, flow through the magnetic coils consisting of the motor stators 1a, rotating motive energy acts on the polar anisotropic permanent magnets 5a, thereby causing the sleeve 5 and the impeller vanes 6 to rotate as a motor rotor.

Then, the front tip portion of the sleeve 5 houses a ring-shaped permanent magnet 5b therein, and at the same time, the fixed body 8 houses a permanent magnet 8a, having a rear surface thereof face toward the front surface of the permanent magnet 5b, therein. At this time, because the magnetic pole of the front side surface of the permanent magnet 5b and the magnetic pole of the rear side surface of the permanent magnet 8a have the same polar character, magnetic forces of repulsion by the permanent magnets 5b and 8a act. The permanent magnets 5b and 8a function, serving as thrust bearings against the axial direction of the central axis X; and the magnetic forces of repulsion by the permanent magnets 5b and 8a are adjusted so as to balance the hydro thrust load that serves as a force to move the sleeve 5 forward, by having the pressure on the more rear side than the impeller vanes 6 become high during operation of the artificial heart pump.

Figure 2:
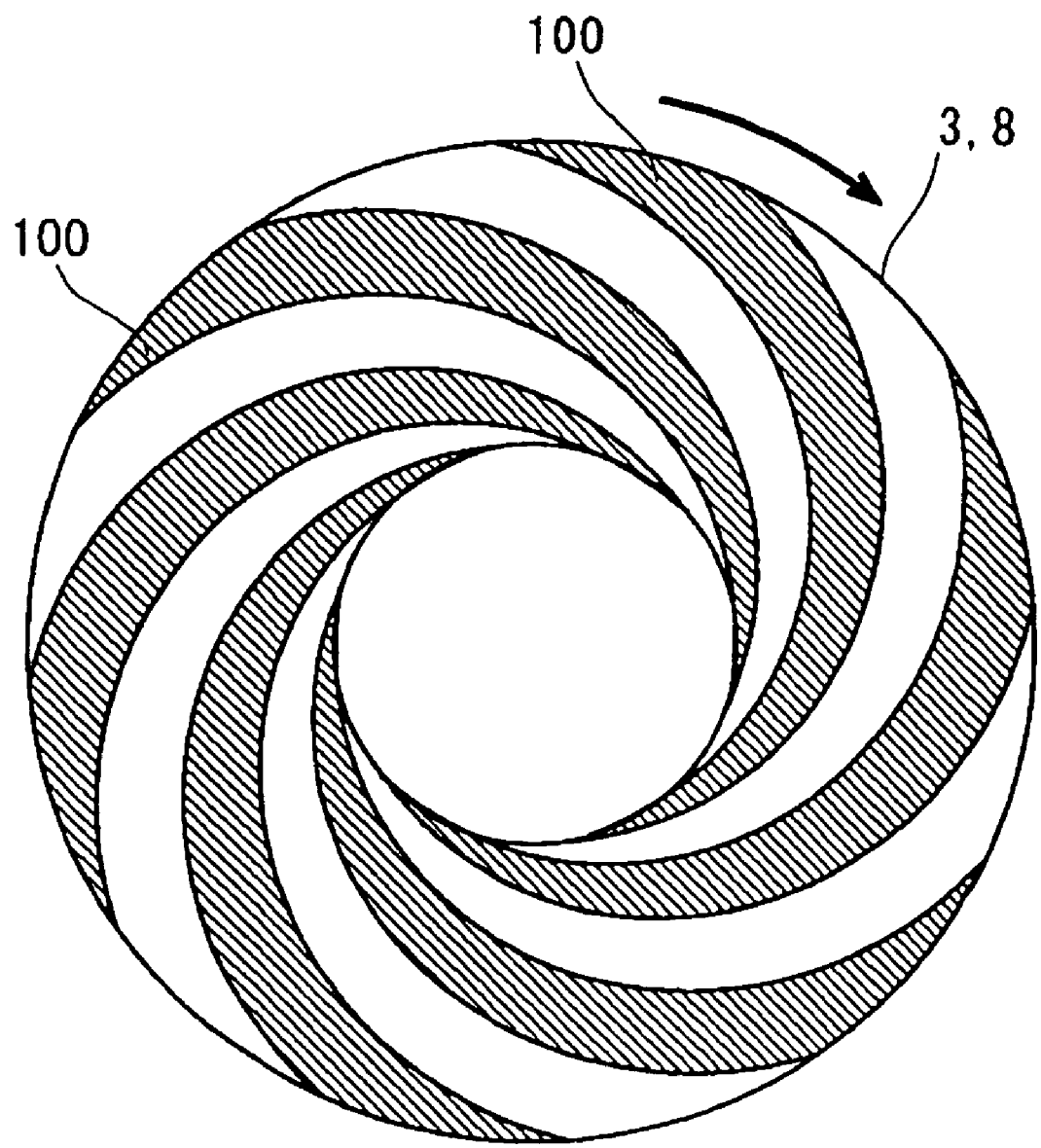
FIG. 2 is a diagram showing a configuration of a thrust hydrodynamic pressure generating groove in an artificial heart pump in FIG. 1

In addition, the front end surface 3x of the fixed body 3 and the rear end surface 8x of the fixed body 8 have a plurality of spiral grooves for generation of thrust hydrodynamic pressure 100, as shown in FIG. 2, formed thereon, respectively. To be specific, hydrodynamic pressures are generated in the blood flowing in the grooves for generation of thrust hydrodynamic pressure 100, so as to support the thrust load being applied to the sleeve 5, together with magnetic forces of repulsion by the permanent magnets 5b and 8a. By the hydrodynamic bearings being constructed by the above-mentioned grooves for generation of thrust hydrodynamic pressure 100 and the passive type of repulsive magnetic bearings being constructed by the permanent magnets 5b and 8a, it is possible to prevent the rear end surface 5x of the sleeve 5 from coming into contact with the front end surface 3x of the fixed body 3, and to prevent the front end surface 5y of the sleeve 6 from coming into contact with the rear end surface 8x of the fixed body 8, when the sleeve 5 rotates.

Moreover, the stationary vanes 7 sticking out from the outside wall surface of the fixed body 8 are placed in a circumferential direction so as to be equally spaced, with the central axis X serving as the center; and additionally, the diffuser vanes 2 having both edges thereof connected to the outside wall surface of the fixed body 3 and to the inside wall surface of the housing 1 are placed in the circumferential direction so as to be equally spaced, with the central axis X serving as the center. Then, the front end of the fixed body 8 and the rear end of the fixed body 3 have the central portions thereof elevated, respectively. In consequence, the bloods being taken in are diverged without receiving any resistance, so as to be led to the stationary vanes 7 by the elevation on the front end of the fixed body 8; and then, the bloods that are flowing, being straightened by the diffuser vanes 2, are led so as to join without receiving any resistance by the elevation on the rear end of the fixed body 3. Moreover, the impeller vanes 6 that stick out from the outside wall surface of the sleeve 5 are placed in the circumferential direction so as to be equally spaced, with the central axis X serving as the center.

Furthermore, the fixed bodies 3 and 8 and the fixed shaft 4 are connected, by inserting a protruding portion 8b, which is provided to the center position of the rear end surface 8x of the fixed body 8, into the hole 4a that is provided to the center position of an end surface 4x on the side of fixed body 8 of the fixed shaft 4 that is connected to the fixed body 3. By having the hole 4a and the protruding portion 8b thread cut, respectively, and by having the protruding portion 8b rotated so as to be inserted into the hole 4a, the fixed body 8 is fixed to the fixed shaft 4, around which the sleeve 5 is installed.

In such an artificial heart pump as described hereinabove, first of all, after the fixed body 3 having the fixed shaft 4 connected thereto is inserted into the housing 1, the outer edges of the diffuser vanes 2 sticking out from the fixed body 3 are connected to the housing 1, and thereby, the fixed body 3 and the fixed shaft 4 are fixed to the inside of the housing 1. Then, after the sleeve 5 which is provided with the impeller vanes 6 on the outer circumference thereof is installed in such a manner as to go around the fixed shaft 4, the fixed body 8 is fixed to the fixed shaft 4, and at the same time, the sleeve 5 is installed between the fixed bodies 3 and 8, by rotating the fixed body 8 while inserting the protruding portion 8b of the fixed shaft 8 into the hole 4a of the fixed shaft 4.

In consequence, the stationary vanes 7 that are connected to the fixed body 8 are put in a condition so as not to be fixed to the housing 1, and in addition, the fixed body 8 and the fixed shaft 4 are connected by a thread connection. As a result, being compared with a conventional fixing manner, the fixed body 8 is easy to be fixed, which enhances the assembly quality thereof. Moreover, when the sleeve 5 being equipped with the impeller vanes 6 is going to be disassembled for an internal inspection and the like, all that is needed to do is to dismantle only the fixed body 8 and take it out of the housing 1. Therefore, it is not necessary to take both fixed bodies 3 and 8 having the fixed shaft 4, around which the sleeve 5 is installed, connected thereto out of the housing 1 as in a conventional manner.

Figure 3:
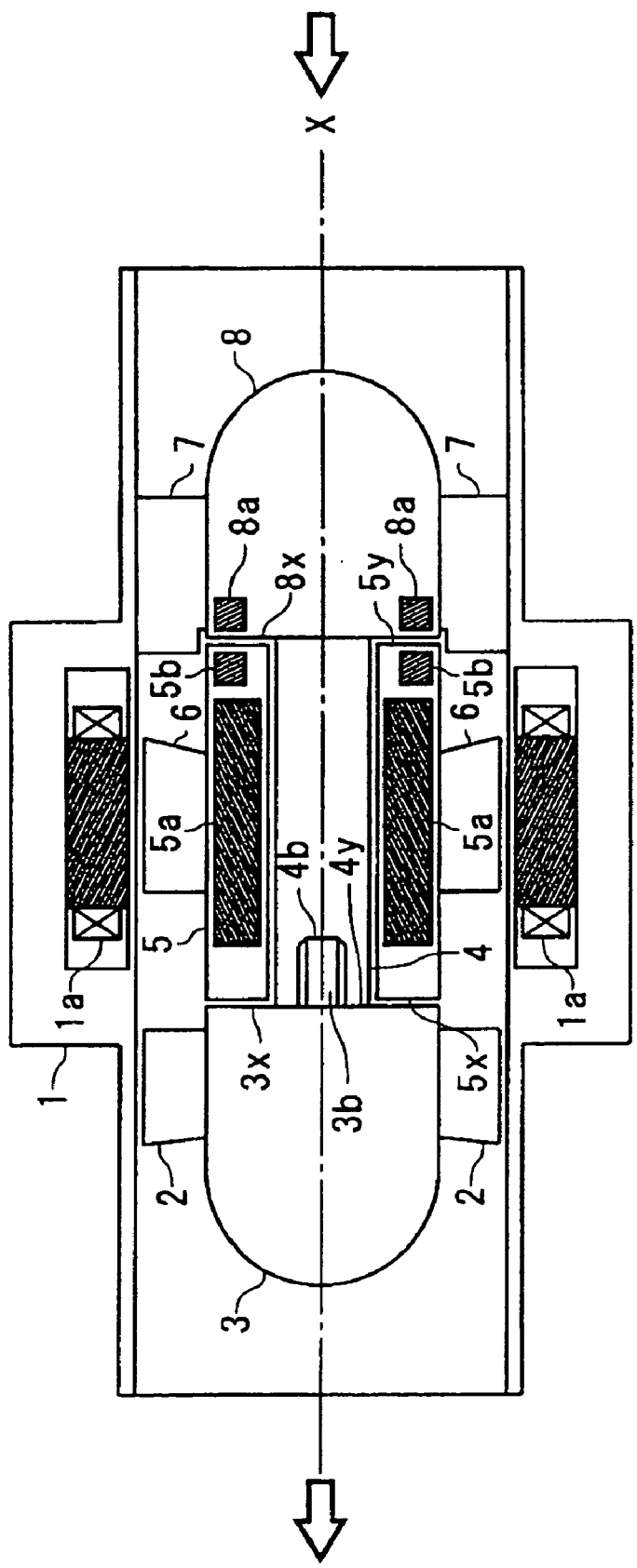
FIG. 3 is a cross-sectional view showing another configuration of an artificial heart pump in accordance with the first embodiment of the present invention.

Moreover, in accordance with the present embodiment, the fixed body 8 that is provided with the stationary vanes 7 is inserted into the fixed shaft 4 so as to be fixed. However, as shown in FIG. 3, the outer edges of the stationary vanes 7 may be connected to the inside wall surface of the housing 1 so as to have the fixed body 8 fixed, and there may exist gaps between the diffuser vanes 2 and the inside wall surface of the housing 1. At this time, the fixed bodies 3 and 8 and the fixed shaft 4 are connected by inserting the protruding portion 3b, which is provided to the center position of the front end surface 3x of the fixed body 3, into the hole 4b which is provided to the center position of the end surface 4y on the side of the fixed body 4 of the fixed shaft 4 being connected to the fixed body 8. The hole 4b and the protruding portion 3b are formed to be thread cut, respectively, and by having the protruding portion 3b rotate so as to be inserted into the hole 4b, the fixed body 3 is fixed to the fixed shaft 4 around which the sleeve 5 is installed.

Figure 4A:
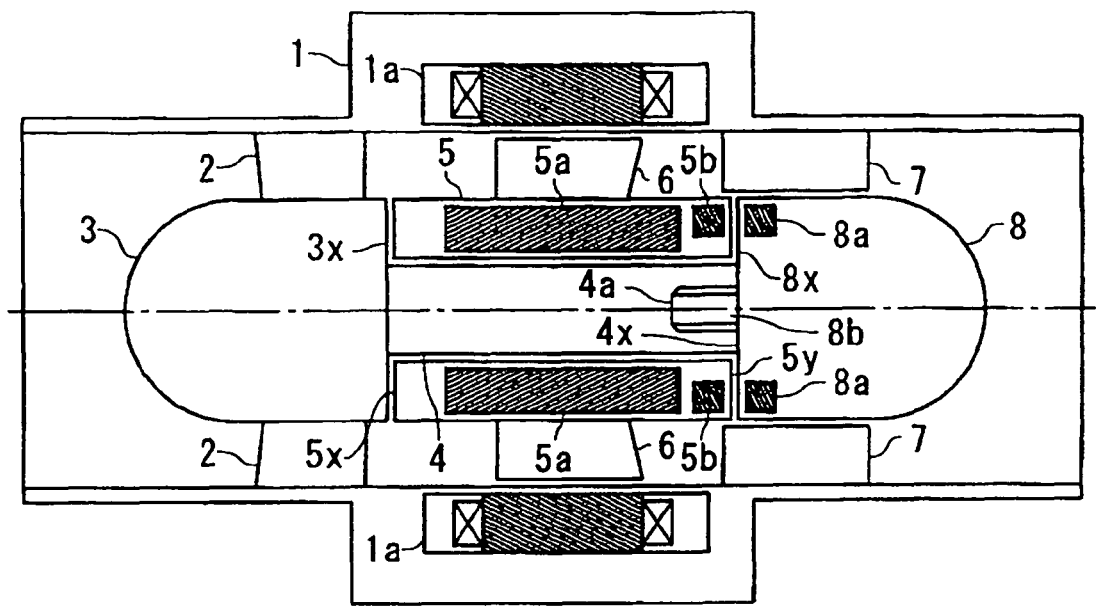
FIG. 4A is a cross-sectional view showing another configuration of an artificial heart pump in accordance with the first embodiment of the present invention.
Figure 4B:
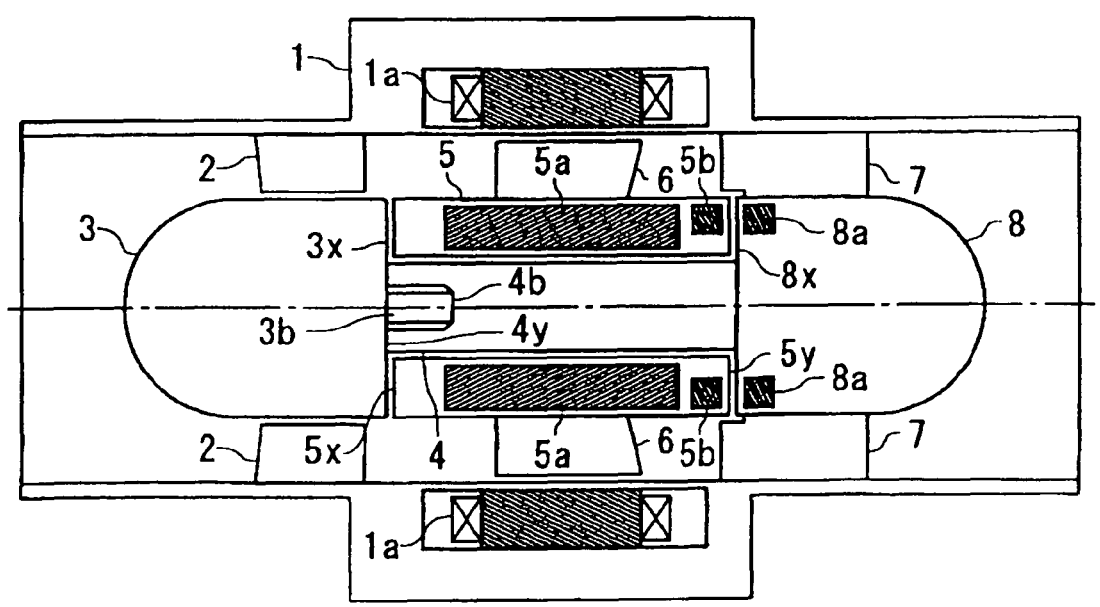
FIG. 4B is a cross-sectional view showing another configuration of an artificial heart pump in accordance with the first embodiment of the prevent invention.

In addition, the inner edges of the stationary vanes 7 are connected to the fixed body 8, and at the same time, the outer edges of the stationary vanes 7 are separated from the housing 1. However, as shown in FIG. 4A, the outer edges of the stationary vanes 7 may be connected to the inside wall surface of the housing 1 so as to be fixed in such a manner as to stick out from the inside wall surface of the housing 1, and the inner edges of the stationary vanes 7 may be separated from the fixed body 8. Similarly, as shown in FIG. 4B, in a case where the fixed body 8 is fixed by having the outer edges of the stationary vanes 7 connected to the inside wall surface of the housing 1 in a same manner as the artificial heart pump shown in FIG. 3, the outer edges of the diffuser vanes 2 may be connected to the inside wall surface of the housing 1 so as to be fixed in such a manner as to stick out from the inside wall surface of the housing 1, and the inner edges of the diffuser vanes 2 may be separated from the fixed body 3.

Figure 5A:
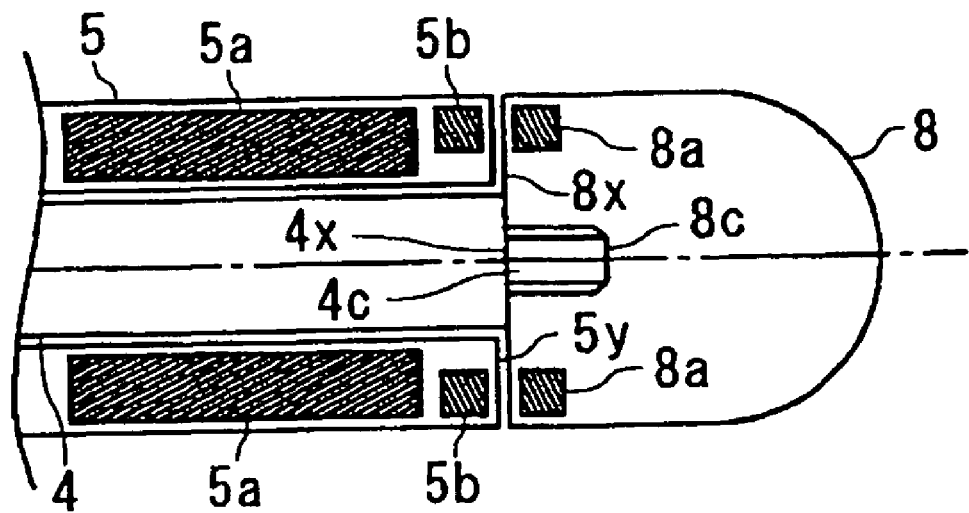
FIG. 5A is a cross-sectional view of a part of an artificial heart pump showing another configuration of the first embodiment of the present invention.
Figure 5B:
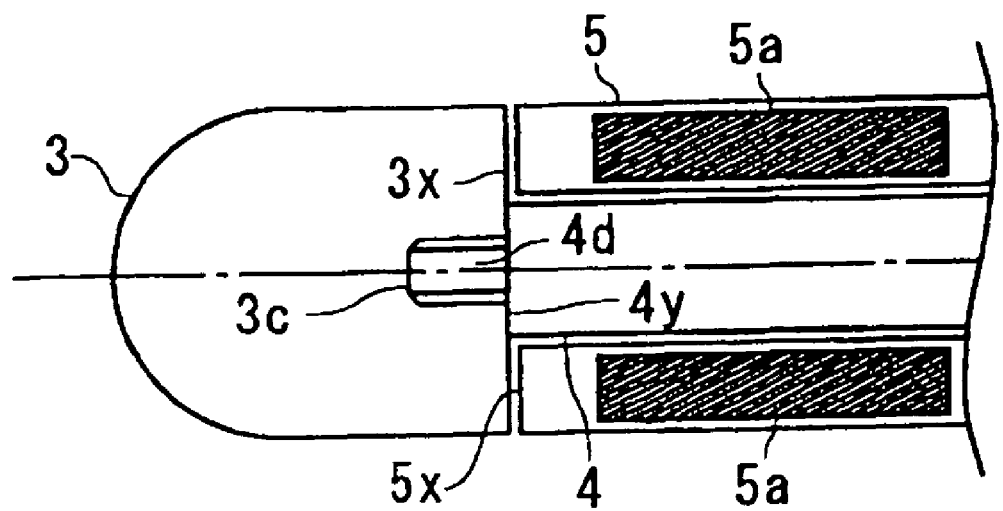
FIG. 5B is a cross-sectional view of a part of an artificial heart pump showing another configuration of the first embodiment of the present invention.

Furthermore, in artificial heart pumps shown in FIG. 1 and FIG. 4A, the fixed body 8 is provided with a protruding portion 8b and fixed by having the protruding portion 8b inserted into the hole 4a of the fixed shaft 4. However, as shown in FIG. 5A, a protruding portion 4c may be provided to the center position of the end surface 4x on the side of the fixed body 8 of the fixed shaft 4, and a hole 8c, which the protruding portion 4c is inserted into, may be provided to the center position of the rear end surface 8x of the fixed body 8. Similarly, as shown in FIG. 5B, in a same manner as the artificial heart pump shown in FIG. 3, in the artificial heart pumps in FIG. 3 and FIG. 4B that have the fixed body 8 fixed, by having the outer edges of the stationary vanes 7 connected to the inside wall surface of the housing 1, a protruding portion 4d may be provided to the center position of the end surface 4y on the side of the fixed body 4 of the fixed shaft 4, and a hole 3c which the protruding portion 4d is inserted into may be provided to the center position of the front end surface 3x of the fixed body 3.

Second Embodiment

Figure 6:
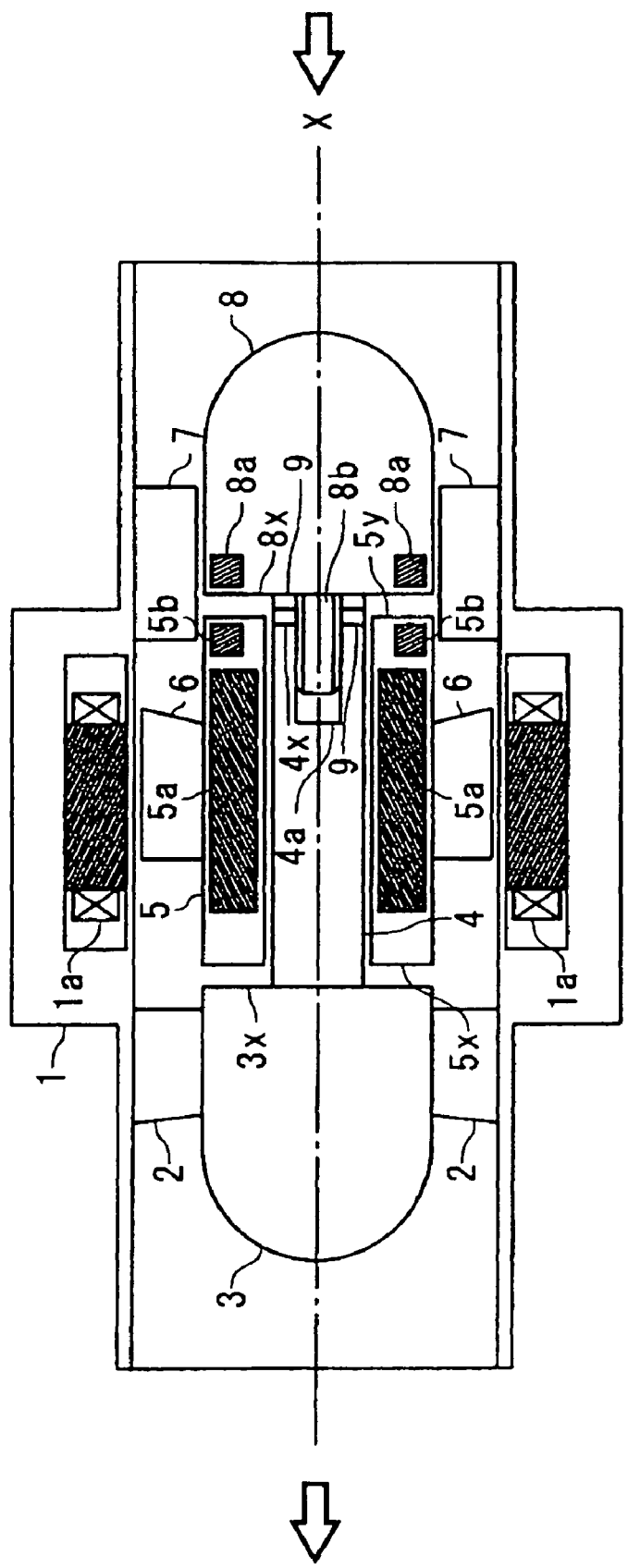
FIG. 6 is a cross-sectional view showing configuration of an artificial heart pump in accordance with a second embodiment of the prevent invention.

Referring to the drawings, a second embodiment of the present invention will be described hereinafter. FIG. 6 is a cross-sectional view showing a configuration of an artificial heart pump in accordance with the present embodiment. In FIG. 6, same portions as in FIG. 1 will be provided with same symbols, and the detailed description thereof will be omitted.

In addition to a configuration of the artificial heart pump in FIG. 1, an artificial heart pump in FIG. 6 has more than one adjustment ring 9, which adjusts a gap between the front end surface 5y of the sleeve 5 and the rear end surface 8x of the fixed body 8, installed between the rear end surface 8x of the fixed body 8 and the front end surface 4x of the fixed shaft 4. At this time, by having the adjustment rings 9 installed around each protruding portion 8b of the fixed body 8, respectively, and by inserting the fixed body 8, around which the adjustment rings 9 are installed, into the hole 4a of the fixed shaft 4, the gap between the fixed body 3 and the sleeve 5 and the gap between the fixed body 8 and the sleeve 5 are adjusted. To be specific, by performing a trial operation during manufacturing, and by measuring the contacts between the fixed bodies 3 and 8 and the sleeve 5, the gap between the fixed body 3 and the sleeve 5 and the gap between the fixed body 8 and the sleeve 5 are confirmed. Subsequently, by adjusting the distance between the fixed bodies 3 and 8 by the number of pieces of the adjustment rings 9 to be installed between the fixed shaft 4 and the fixed body 8, the gap between the fixed body 3 and the sleeve 5 and the gap between the fixed body 8 and the sleeve 5 are adjusted.

In addition, in accordance with the present embodiment, the adjustment rings 9 are added to the configuration of the artificial heart pump in FIG. 1. However, the adjustment rings 9 may be added to the configuration of the artificial heart pump in FIG. 4A. At this time, same as shown in FIG. 6, the adjustment rings 9 are installed around the protruding portion 8b of the fixed body 8, and the protruding portion 8b is inserted into the hole 4a of the fixed shaft 4. Moreover, the adjustment rings may be added to the configuration of the artificial heart pumps in FIG. 3 and FIG. 4B, and the protruding portion 3b of the fixed body 3, which the adjustment rings 9 may be installed around, may be inserted into the hole 4b of the fixed shaft 4. Additionally, as the artificial heart pumps in FIG. 5A and FIG. 5B, the fixed shaft 4 may be provided with protruding portions 4c and 4d, and the protruding portions 4c and 4d may have the adjustment rings 9 installed around, and may be inserted into the hole 8c of the fixed body 8 and the hole 3c of the fixed body 3.

Third Embodiment

Figure 7:
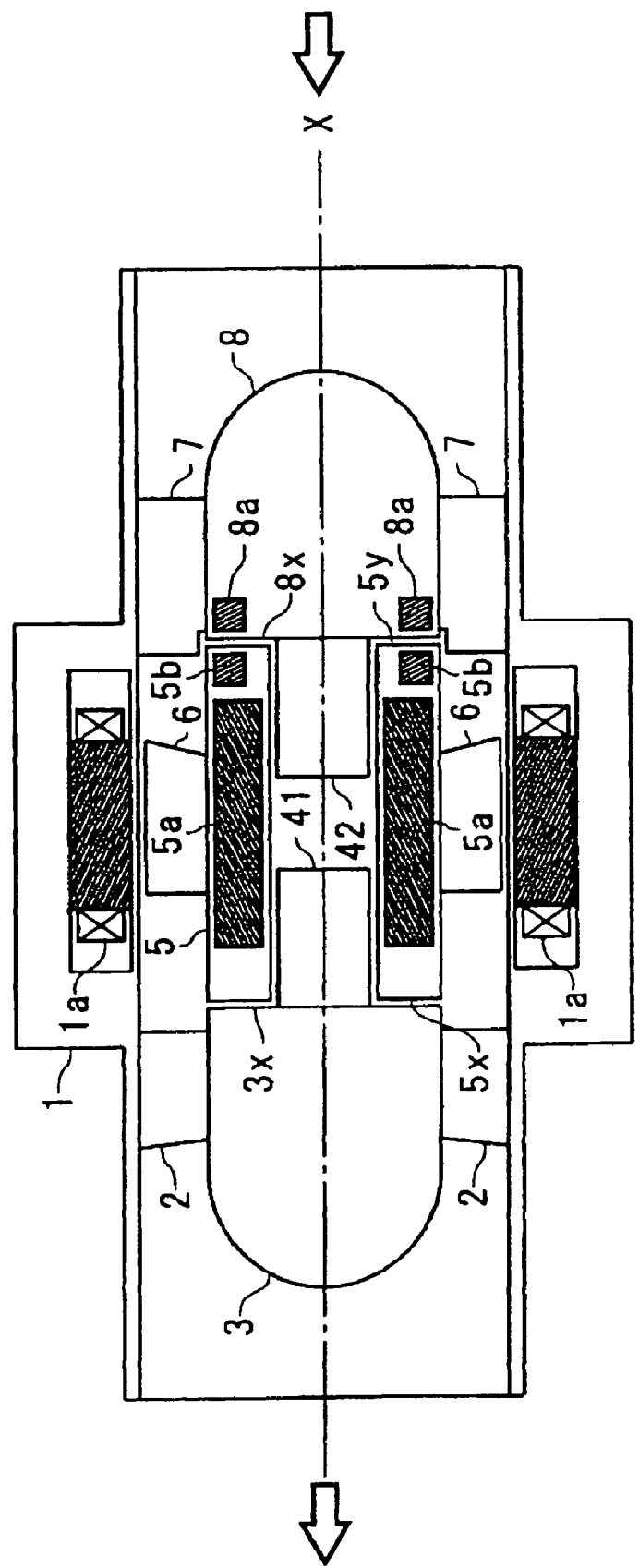
FIG. 7 is a cross-sectional view showing a configuration of an artificial heart pump in accordance with a third embodiment of the prevent invention.

Referring to the drawings, a third embodiment of the present invention will be described hereinafter. FIG. 7 is a cross-sectional view showing a configuration of an artificial heart pump in accordance with the present embodiment. In FIG. 7, same portions as in FIG. 1 will be provided with same symbols, and the detailed description thereof will be omitted.

In the artificial heart pump in FIG. 7, being different from the artificial heart pump in FIG. 1, the outer edges of the stationary vanes 7 are connected to the inside wall surface of the housing 1 so a to have the fixed body 8 fixed, and the fixed shaft 4 is divided into two fixed shafts 41 and 42, which are connected to the fixed bodies 3 and 8, respectively. In this artificial heart pump, first of all, after the fixed body 3 being equipped with the diffuser vanes 2 is fixed inside the housing 1 by having the outer edges of the diffuser vanes 2 fastened to the inside wall surface of the housing 1, the sleeve 5 being equipped with the impeller vanes 6 is installed around the fixed shaft 41 that is connected to the fixed body 3. Then, the fixed body 8 is installed inside the housing 1 by inserting the fixed shaft 42 which is connected to the fixed body 8, into the hole in the sleeve 5.

When the fixed bodies 3 and 8 and the sleeve 5 are installed inside the housing 1, respectively, in such a manner as described hereinabove, the gap between the fixed body 3 and the sleeve 5 and the gap between the fixed body 8 and the sleeve 5 are confirmed by performing a trial operation and measuring the contacts of the fixed bodies 3 and 8 with the sleeve 5. Subsequently, when the position to install the fixed body 8 is shifted in the direction of the X-shaft to be changed and is specified so as to adjust the gap between the fixed body 3 and the sleeve 5 and the gap between the fixed body 8 and the sleeve 5 that are already confirmed, the fixed body 8 is fixed inside the housing 1 by having the outer edges of the stationary vanes 7 fastened to the inside wall surface of the housing 1. By shifting the fixed body 8 in the direction of the X-shaft in such a manner as has been described hereinabove, the distance between the fixed bodies 3 and 8 can be adjusted simply, thereby making it possible to adjust the gap between the fixed body 3 and the sleeve 5 and the gap between the fixed body 8 and the sleeve 5 to have an appropriate distance. In addition, in accordance with the present embodiment, an adjustment can be made by fixing the fixed body 3 and shifting the fixed body 8. However, an adjustment may be made by fixing the fixed body 8 and shifting the fixed body 3.

Moreover, in dismantling the sleeve 5, which is equipped with the impeller vanes 6, for an internal inspection and the like, all that has to be done is to simply disassemble only one of the fixed bodies 3 and 8 to take out of the housing 1. Therefore, it is unnecessary to dismantle both fixed bodies 3 and 8, that have the fixed shaft 4, having a sleeve 5 installed around, connected thereto, from the housing 1.

Fourth Embodiment

Figure 8:
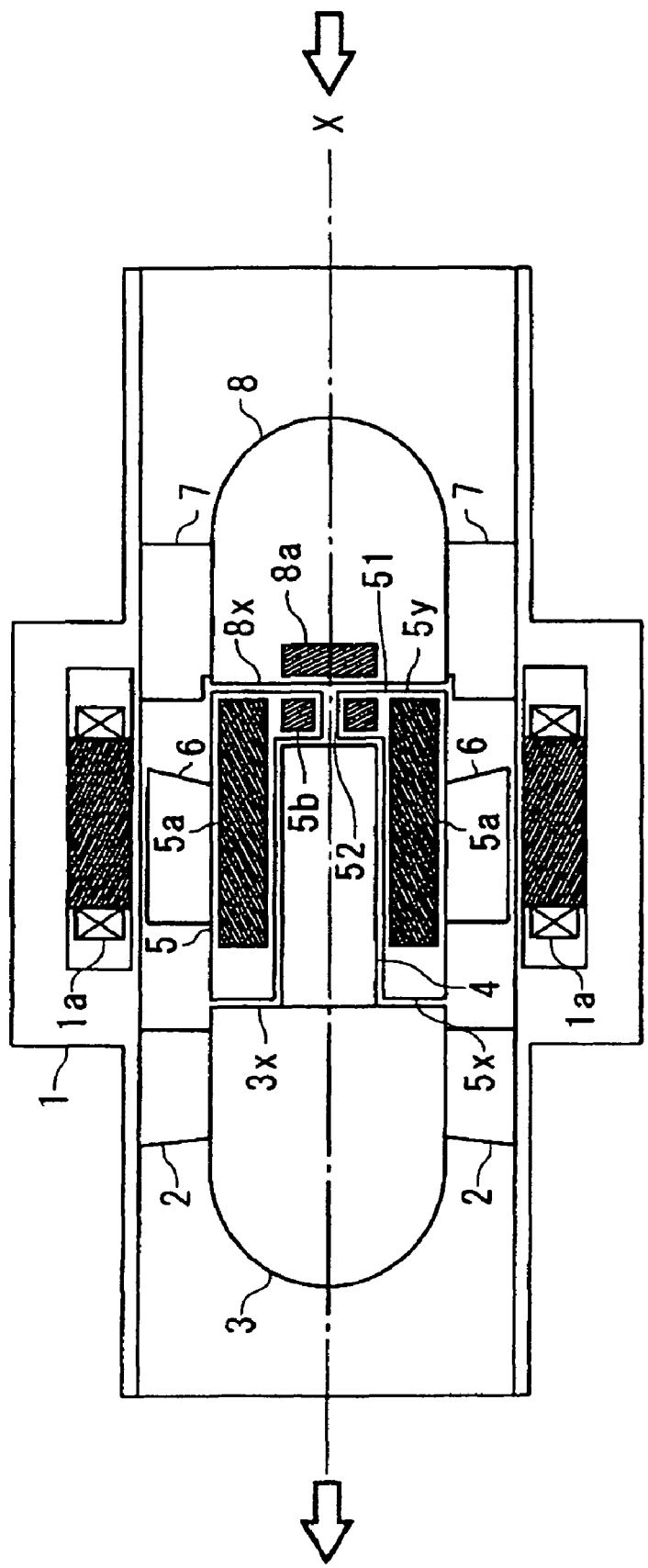
FIG. 8 is a cross-sectional view showing a configuration of an artificial heart pump in accordance with a fourth embodiment of the prevent invention.

Referring to the drawings, a fourth embodiment of the present invention will be described hereinafter. FIG. 8 is a cross-sectional view showing a configuration of an artificial heart pump in accordance with the present embodiment. In FIG. 8, same portions as in FIG. 1 will be provided with same symbols, and the detailed description thereof will be omitted.

Being different from the artificial heart pump in FIG. 1, the artificial heart pump in FIG. 8 has the fixed shaft 4 connected only to the fixed body 3, and has the sleeve 5 provided with the bottom portion 51 at such a location as to intervene between the fixed shaft 4 and the fixed body 8. Then, a ring-shaped permanent magnet 5b is housed inside the bottom portion 51 of the sleeve 5. The permanent magnet 5b is installed so as to be located more inside than the polar anisotropic permanent magnet 5a. To be specific, the diameter of the outer circumference of the permanent magnet 5b is smaller than the diameter of the inner circumference of the polar anisotropic permanent magnet 5a; and the permanent magnet 5b is installed so as to overlap at the front end of the polar anisotropic permanent magnet 5a in the direction of the X-shaft.

In addition, a cylindrical permanent magnet 8a is installed to a position facing toward the permanent magnet 5b inside the fixed body 8. At this time, since the magnetic pole of the front side surface of the permanent magnet 5b and the magnetic pole of the rear side surface of the permanent magnet 8a have the same polar character, magnetic forces of repulsion by the permanent magnets 5b and 8a work. Moreover, a through hole 52 is provided to the center position of the bottom portion 51 of the sleeve 5, and by way of the through hole 52, the blood that flows into the gap between the inner circumference wall of the sleeve 5 and the outer circumference wall of the fixed shaft 4 is discharged, and thereby, the blood can be prevented from clotting.

Figure 9:
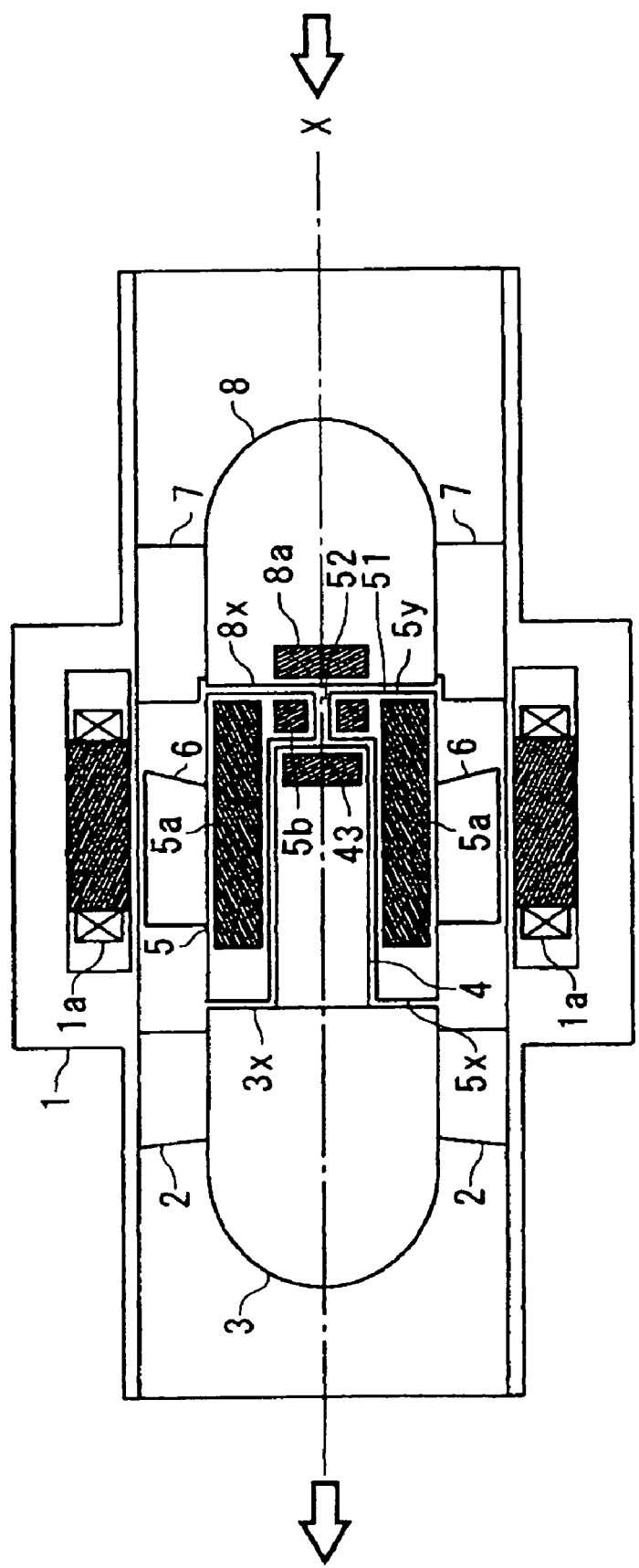
FIG. 9 is a cross-sectional view showing another configuration of an artificial heart pump in accordance with the fourth embodiment of the prevent invention.

As has been described hereinabove, in accordance with the configuration of the present embodiment, the permanent magnet 5b that serves as a part of a passive type of the repulsive magnetic bearing can be installed at such a position as to overlap the polar anisotropic permanent magnet 5a in the axial direction, so that the axial length of the sleeve 5 can be such a length as depends only on the polar anisotropic permanent magnet 5a. In addition, as shown in FIG. 9, a permanent magnet 43 that generates a magnetic force acting repulsively against a magnetic force that is generated on the rear side of the permanent magnet 5b may be housed inside the front side tip of the fixed shaft 4. By having such a configuration as has been described, the front side tip of the fixed shaft 4 can be prevented from coming into contact with the inside wall surface of the bottom portion 51 of the sleeve 5, and at the same time, the fixed body 3 can be prevented from coming into contact with the sleeve 5.

Fifth Embodiment

Figure 10:
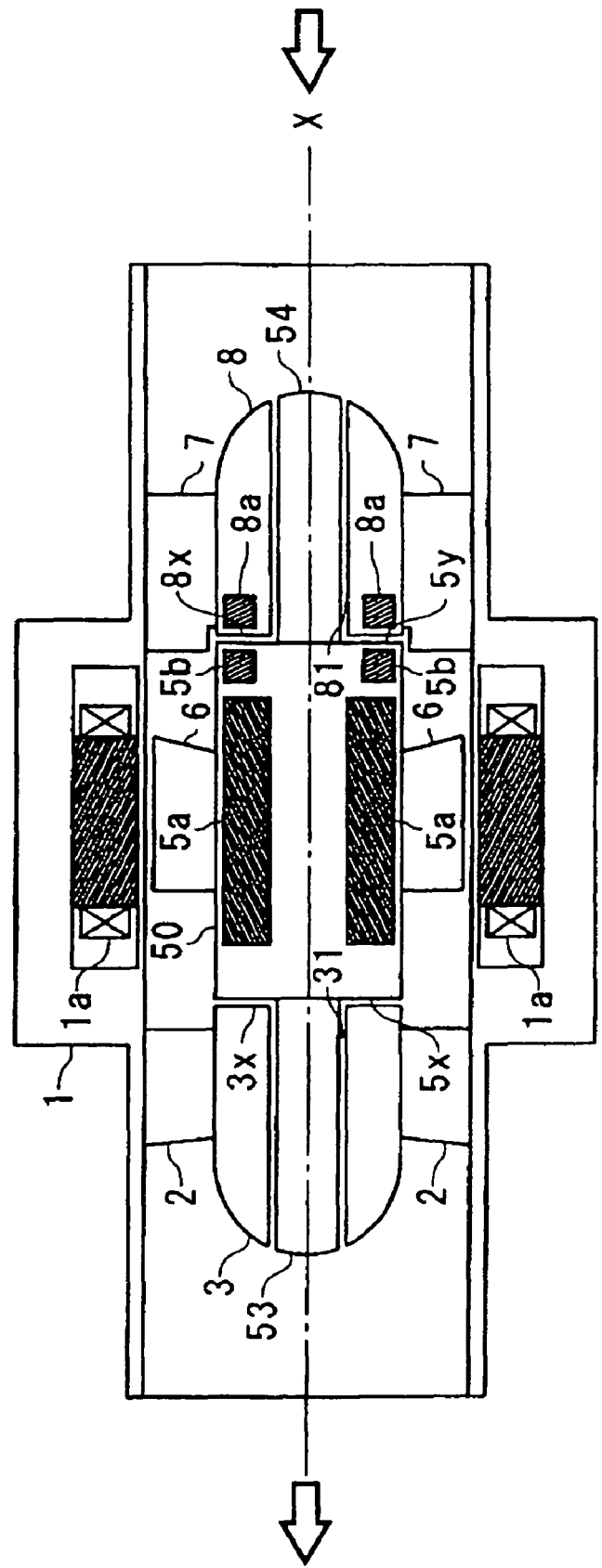
FIG. 10 is a cross-sectional view showing a configuration of an artificial heart pump in accordance with a fifth embodiment of the prevent invention.

Referring to the drawings, a fifth embodiment of the present invention will be described hereinafter. FIG. 10 is a cross-sectional view showing a configuration of an artificial heart pump in accordance with the present embodiment. In FIG. 10, same portions as in FIG. 1 will be provided with same symbols, and the detailed description thereof will be omitted.

In the artificial heart pump shown in FIG. 10, being different from the artificial heart pump in FIG. 1, through holes 31 and 81 that run through in the direction of the X-shaft are provided to the center positions of the fixed bodies 3 and 8, instead of the fixed shaft 4 and the sleeve 5 that function so as to serve as journal bearings; and at the same time, such a impeller 50 is provided as has the main shafts 53 and 54, that are inserted into the through holes 31 and 81 in the fixed bodies 3 and 8, respectively, connected to both ends thereof in the direction of the X-shaft. To be specific, by having the main shafts 53 and 54 inserted into the through holes 31 and 81, the through holes 31 and 81 and the main shafts 53 and 54 function so as to serve as the journal bearings; the impeller vanes 6 are installed to the outer circumference wall of the impeller 50, being equally spaced, so as to stick out; and the impeller 50 houses the polar anisotropic permanent magnet 5a and the permanent magnet 5b therein in the same manner as the sleeve 5.

Moreover, the rear end surface of the main shaft 53 and the front end surface of the main shaft 54 have the center portions thereof elevated, respectively. Then, each of the rear side end portion of the fixed body 3 and the front side end portion of the fixed body 8 is formed to be a curved surface that continues to each curved surface of the rear side end surface of the main shaft 53 and the front side end surface of the main shaft 54, respectively. As a result, the blood that is taken in by the elevation of the main shaft 54 and the curved surface on the front side of the fixed body 8 can be diverged without resistance so as to be led to the stationary vanes 7; and the blood that flows, being straightened by the diffuser vanes 2, is led by the curved surface on the rear side of the fixed body 3 and the elevation of the main shaft 53 so as to be joined without resistance.

As described hereinabove, being different from the other embodiments in which the sleeve 5 having the impeller vanes 6 stick out serves as a rotating body, in accordance with the present embodiment, the impeller 50, which is provided with the main shafts 53 and 54 and has the impeller vanes 6 stick out, serves as a rotating body, and thereby a rotating shaft 4 is not necessary, while it is necessary in accordance with the other embodiments. In consequence, being compared with the artificial heart pumps in accordance with the other embodiments, since the locations to install the polar anisotropic permanent magnet 5a and the permanent magnet 5b can be shifted toward the inside diameter, the outside diameter of the impeller 50 in the artificial heart pump in accordance with the present embodiment can be made smaller than the outside diameter of the sleeves 5 of the artificial heart pumps in accordance with the other embodiments, and thereby, the radial configuration of the artificial heart pump can be downsized.

Sixth Embodiment

Figure 11:
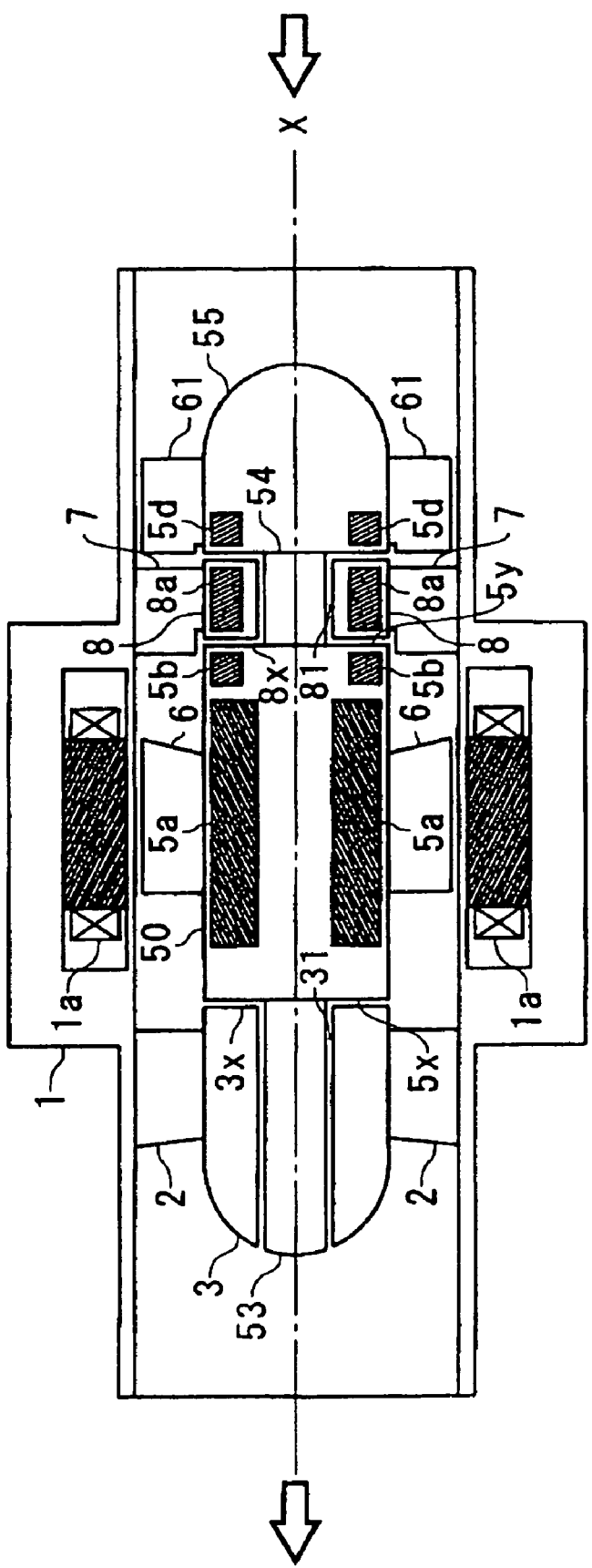
FIG. 11 is a cross-sectional view showing a configuration of an artificial heart pump in accordance with a sixth embodiment of the prevent invention.

Referring to the drawings, a sixth embodiment of the present invention will be described hereinafter. FIG. 11 is a cross-sectional view showing a configuration of an artificial heart pump in accordance with the present embodiment. In FIG. 11, same portions as in FIG. 10 will be provided with same symbols, and the detailed description thereof will be omitted.

The artificial heart pump shown in FIG. 11 includes the impeller 55 that is installed to the front side tip of the main shaft 54; the impeller vanes 61 that stick out from the outside wall surface of the impeller 55; and a ring-shaped permanent magnet 5d that is installed inside the impeller 55, in addition to the configuration of the artificial heart pump in FIG. 10. Moreover, the axial length of the fixed body 8 is approximately the same as the length of the stationary vanes 7, so that being different from the artificial heart pump in FIG. 10, the front side of the fixed body 8 is formed by a flat surface that is in parallel with the rear side thereof. Furthermore, instead of the front side end surface of the main shaft 54 of the artificial heart pump in FIG. 10, the front side end surface of the impeller 55 has the center portion thereof elevated.

Then, the permanent magnet 5d is housed in on the rear side of the impeller 55 so as to counterwork the permanent magnet 8a, and a magnetic force that is generated by the permanent magnet 5d serves as a repulsive magnetic force against a magnetic force that is generated on the front side of the permanent magnet 8a. By having such a configuration as has been described, the front side end surface of the fixed body 8 can be prevented from coming into contact with the rear side end surface of the impeller 55, and at the same time, the rear side end surface of the impeller 50 that is connected to the impeller 55 by the main shaft 54 can be prevented from coming into contact with the front side end surface of the fixed shaft 3.

Moreover, same as the impeller vanes 6, the impeller vanes 61 are installed so as to be equally spaced in the circumferential direction, with the central axis X serving as the center. By the impeller vanes 6 and the impeller vanes 61, is configured an axial-flow pump that consists of two stages, having the stationary vanes 7 intervene between the impeller vanes 6 and the impeller vanes 61 so as to serve as the stationary vanes. By being configured to have two stages in such a manner as mentioned hereinabove, high discharge pressure can be achieved at a low rotating speed, being compared with the artificial heart pumps in accordance with the other embodiments that consist of a single stage. As a result, operation can be possible at a low rotating speed, thereby enhancing the hemolytic property.

Seventh Embodiment

Figure 12:
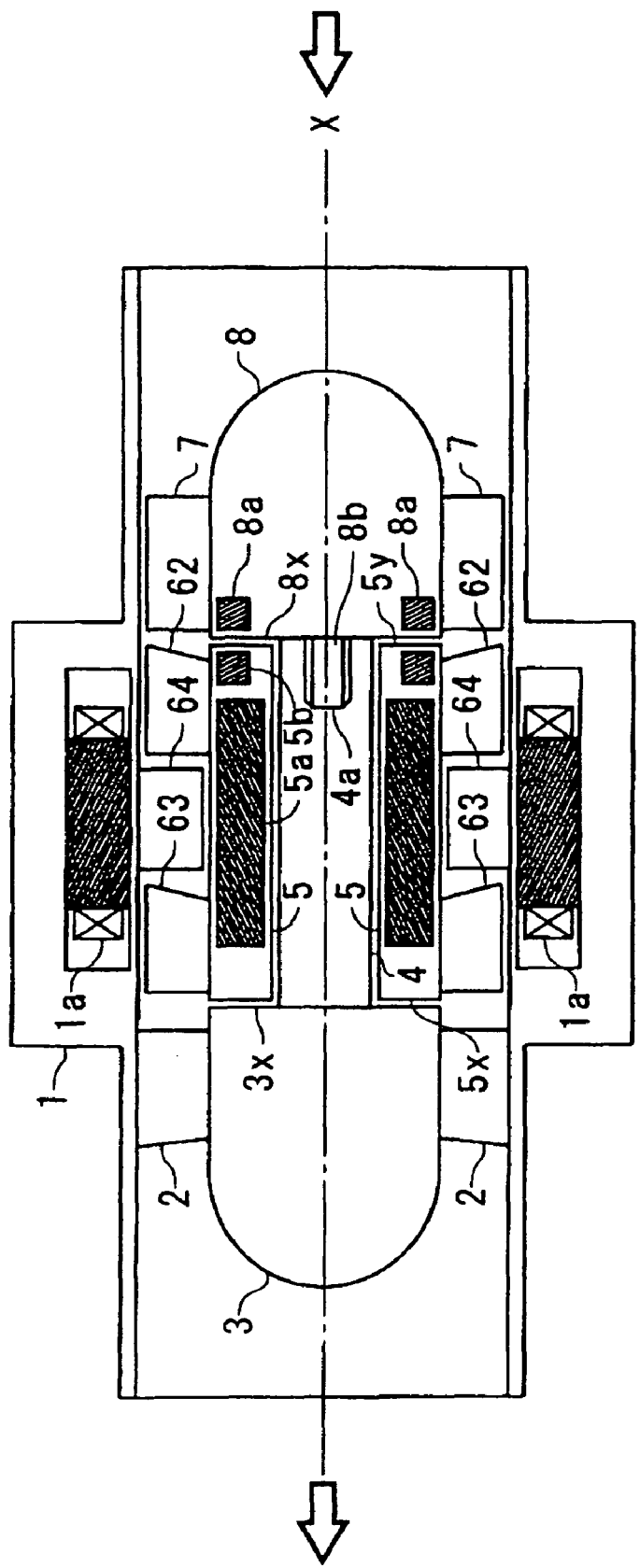
FIG. 12 is a cross-sectional view showing a configuration of an artificial heart pump in accordance with a seventh embodiment of the present invention.

Referring to the drawings, a seventh embodiment of the present invention will be described hereinafter. FIG. 12 is a cross-sectional view showing a configuration of an artificial heart pump in accordance with the present embodiment. In FIG. 12, same portions as in FIG. 1 will be provided with same symbols, and the detailed description thereof will be omitted.

Being different from the artificial heart pump in FIG. 1, the artificial heart pump in FIG. 12 has the impeller vanes 62 and the impeller vanes 63 installed to the front side and the rear side of the sleeve 5, respectively, instead of the impeller vanes 6, so as to stick out from the outside wall surface of the sleeve 5 toward the inside wall surface of the housing 1. The impeller vanes 62 and the impeller vanes 63 are arranged so as to be equally spaced in a circumferential direction, with the central axis X serving as the center. In addition, between the impeller vanes 62 and the impeller vanes 63 are installed the stationary vanes 64 so as to stick out from the inside wall surface of the housing 1 to the outside wall surface of the sleeve 5. The stationary vanes 64 are arranged so as to be equally spaced in a circumferential direction, with the central axis X serving as the center, in the same manner as the impeller vanes 62 and the impeller vanes 63.

As described hereinabove, the artificial heart pump in FIG. 12 is configured so as to be an axial-flow pump that consists of two stages, having the impeller vanes 62 and the impeller vanes 63 installed, intervening the stationary vanes 64 therebetween. By being configured to have two stages in such a manner as described hereinabove, same as the sixth embodiment, high discharge pressure can be achieved at a low rotating speed, being compared with the artificial heart pumps in accordance with the other embodiments that consist of a single stage. As a result, operation can be possible at a low rotating speed, thereby enhancing the hemolytic property.

In addition, the present embodiment has been described based on the configuration in FIG. 1 of the first embodiment. However, the configurations shown in FIG. 3, FIG. 4A, FIG. 4B, FIG. 5A and FIG. 5B may include the impeller vanes 62, the impeller vanes 63 and the stationary vanes 64, instead of the impeller vanes 6, in the similar manner. Moreover, in the same manner as conventional, with the diffuser vanes 2 and the stationary vanes 7 connected to both of the fixed bodies 3 and 8 and the housing 1, the impeller vanes 62, the impeller vanes 63 and the stationary vanes 64 may be provided, instead of the impeller vanes 6.

Furthermore, for the above-mentioned configurations of the second through the fourth embodiments, the impeller vanes 62 and the impeller vanes 63 may be installed to the outside wall surface of the sleeve 5, instead of the impeller vanes 6, and at the same time, the stationary vanes 64 may be installed to the inside wall surface of the housing 1, intervening between the impeller vanes 62 and the impeller vanes 63. Additionally, for the above-mentioned configurations of the fifth and the sixth embodiments, the impeller vanes 62 and the impeller vanes 63 may be installed to the outside wall surface of the impeller 50, instead of the impeller vanes 6, and at the same time, the stationary vanes 64 may be installed to the inside wall surface of the housing 1, intervening between the impeller vanes 62 and the impeller vanes 63.

Figure 13:
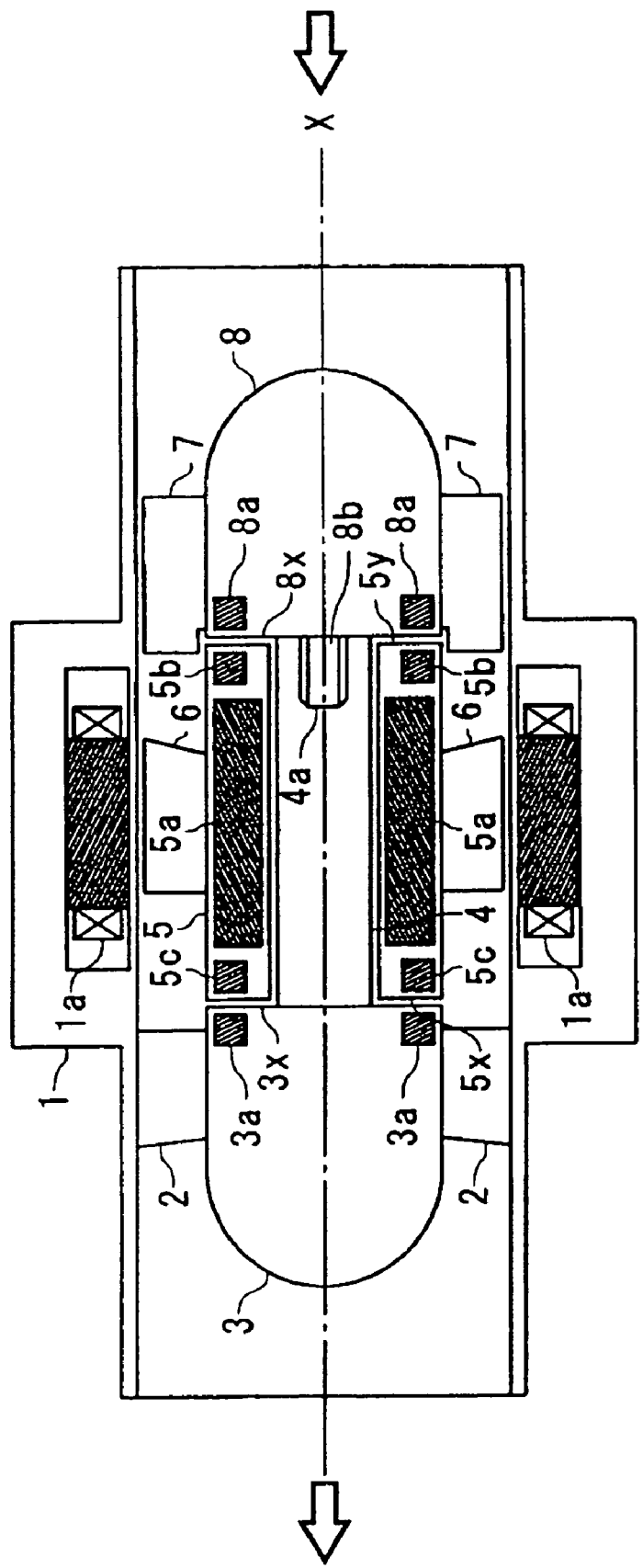
FIG. 13 is a cross-sectional view showing a configuration of an artificial heart pump having a passive type of repulsive magnetic bearings that are installed to both of two fixed bodies.

Moreover, in accordance with the above-mentioned first through the seventh embodiments, passive type of repulsive magnetic bearings are configured by the permanent magnets 5b and 8a that are housed in the sleeve 5 and the fixed body 8. However, as shown in FIG. 13, in addition to the passive type of repulsive magnetic bearings being configured by the permanent magnets 5b and 8a, the sleeve 5 may house a ring-shaped permanent magnet 5c at the rear tip portion thereof, and at the same time, the fixed body 3 may house a permanent magnet 3a therein whose front surface faces toward the rear surface of the permanent magnet 5c. To be specific, the magnetic pole of the rear side surface of the permanent magnet 5c and the magnetic pole of the front side surface of the permanent magnet 3a may have the same polar character, and passive type of repulsive magnetic bearings may be configured by the magnetic forces of repulsion being generated by the permanent magnets 5c and 3a. In addition, FIG. 13 shows a configuration that has the passive type of repulsive magnetic bearings by the permanent magnets 5c and 3a added to the configuration of FIG. 1.

Eighth Embodiment

Figure 14:
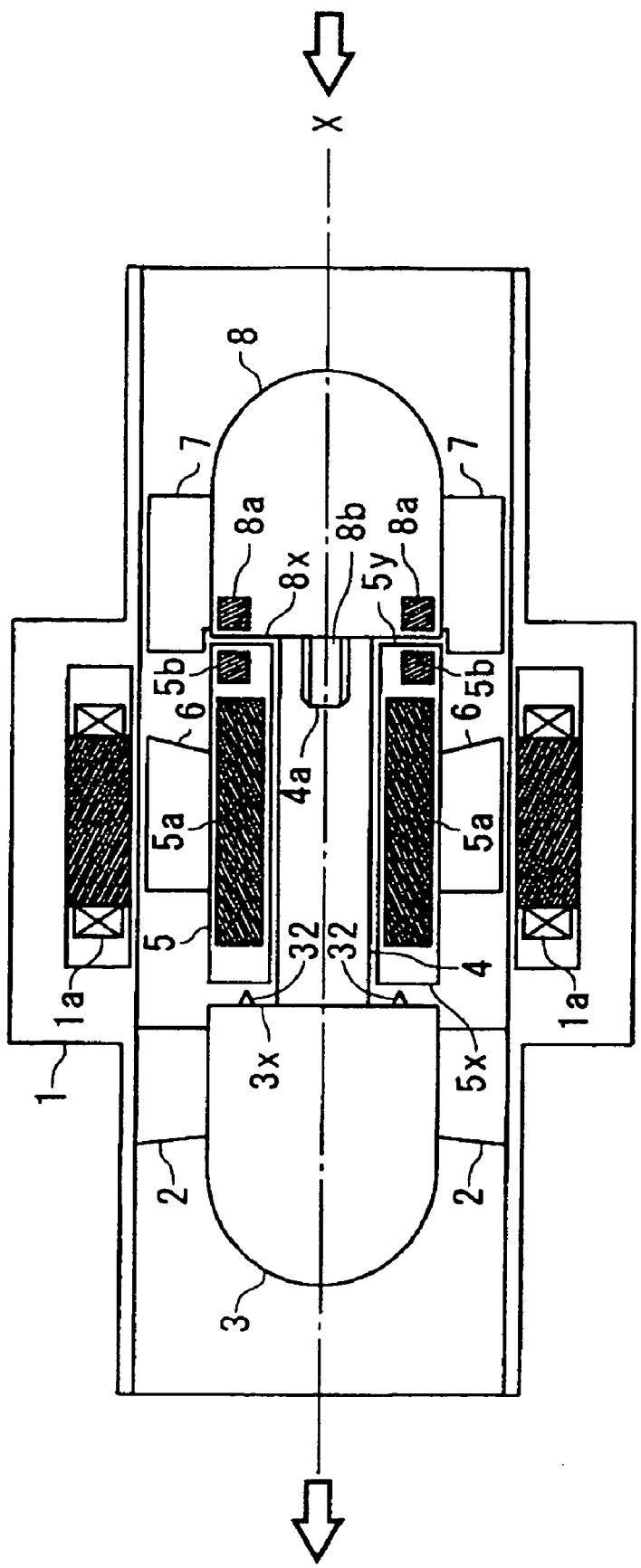
FIG. 14 is a cross-sectional view showing a configuration of an artificial heart pump in accordance with an eighth embodiment of the present invention.

Referring to the drawings, a eighth embodiment of the present invention will be described hereinafter. FIG. 14 is a cross-sectional view showing a configuration of an artificial heart pump in accordance with the present embodiment. In FIG. 14, same portions as in FIG. 1 will be provided with same symbols, and the detailed description thereof will be omitted.

Figure 15:
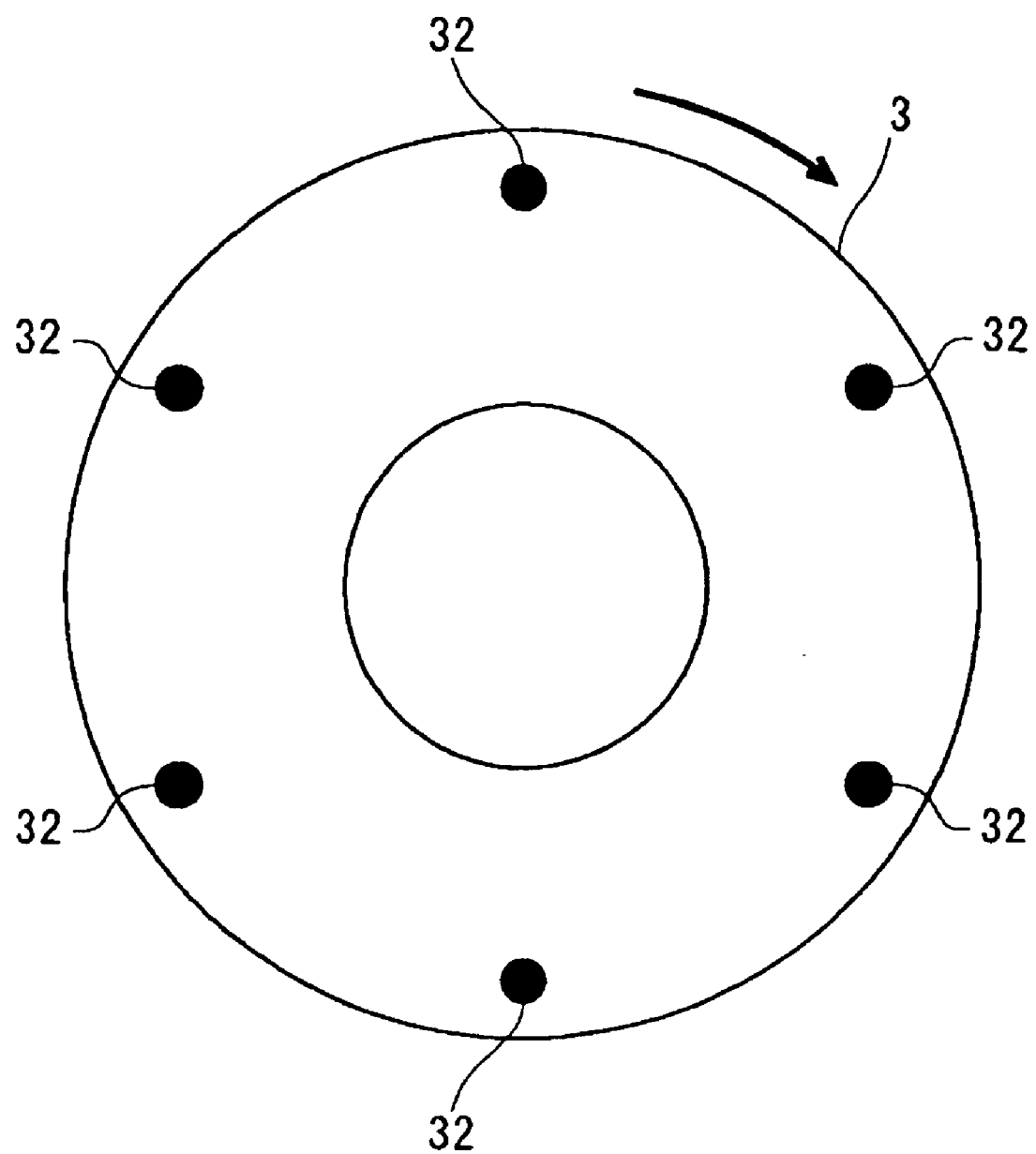
FIG. 15 is a diagram showing positional relations of protruding portions in an artificial heart pump in FIG. 14.

In addition to the configuration of the artificial heart pump in FIG. 1, the artificial heart pump shown in FIG. 14 is configured in a manner that a plurality of protruding portions 32 in a shape of a cone are provided to the front end surface 3x of the fixed body 3 on the outer circumference side of the fixed shaft 4. To be specific, as shown in FIG. 15, the protruding portions 32 are arranged on the front end surface 3x of the fixed body 3 so as to be equally spaced in the circumferential direction of a same radius, with the central axis X serving as the center. Moreover, the protruding portions 32 are shaped in a cone so as to have tops thereof formed on the front side, and the tops thereof come into contact with the rear end surface 5x of the sleeve 5 during rotation at a low rotating speed, such as start-ups, shutdowns and the like.

Same as the first embodiment, when the artificial heart pump that is configured in such a manner as has been described hereinabove performs a normal rotating operation, hydro thrust loads are generated that serve as a force to shift the sleeve 5 forward by having the pressure on more rear side than the impeller vanes 6 increased. Then, by having the magnetic forces of repulsion by the permanent magnets 5b and 8a act so as to balance with the hydro thrust loads, it is possible to prevent the rear end surface 5x of the sleeve 5 from coming into contact with the front end surface 3x of the fixed body 3, and to prevent the front end surface 5y of the sleeve 5 from coming into contact with the rear end surface 8x of the fixed body 8. At this time, although the blood flows into the gap that is formed between the rear end surface 5x of the sleeve 5 and the front end surface 3x of the fixed body 3, the flow of the blood that streams in cannot be interrupted because the protruding portions 32 are arranged with spaces equally provided therebetween.

In addition, since the hydro thrust load is small during start-ups, shutdowns, and the like, the sleeve 5 shifts backward by the magnetic forces of repulsion by the permanent magnets 5b and 8a. Therefore, the rear end surface 5x of the sleeve 5 and the front end surface 3x of the fixed body 3 try to come into contact with each other, and thereby, the rear end surface 5x of the sleeve 5 comes into contact with the tops of the protruding portions 32. By this, when the sleeve 5 shifts backward so as to come into contact with the fixed body 3 during a start-up and a shutdown, the contact occurs only at the tops of the protruding portions 32, which can reduce the contact area. In consequence, an amount of wear during the contact can be restrained, and at the same time, the hemolyzing performance can be prevented from deteriorating.

Furthermore, the present embodiment has been described based on the configuration of the first embodiment shown in FIG. 1. However, the configurations shown in FIG. 3, FIG. 4A, FIG. 4B, FIG. 5A and FIG. 5B may have the protruding portions 32 provided to the front end surface 3x of the fixed body 3 in the similar manner. Additionally, the configurations of the above-mentioned second through the seventh embodiments may have the protruding portions 32 installed to the front end surface 3x of the fixed body 3 in the same manner.

Ninth Embodiment

Figure 16:
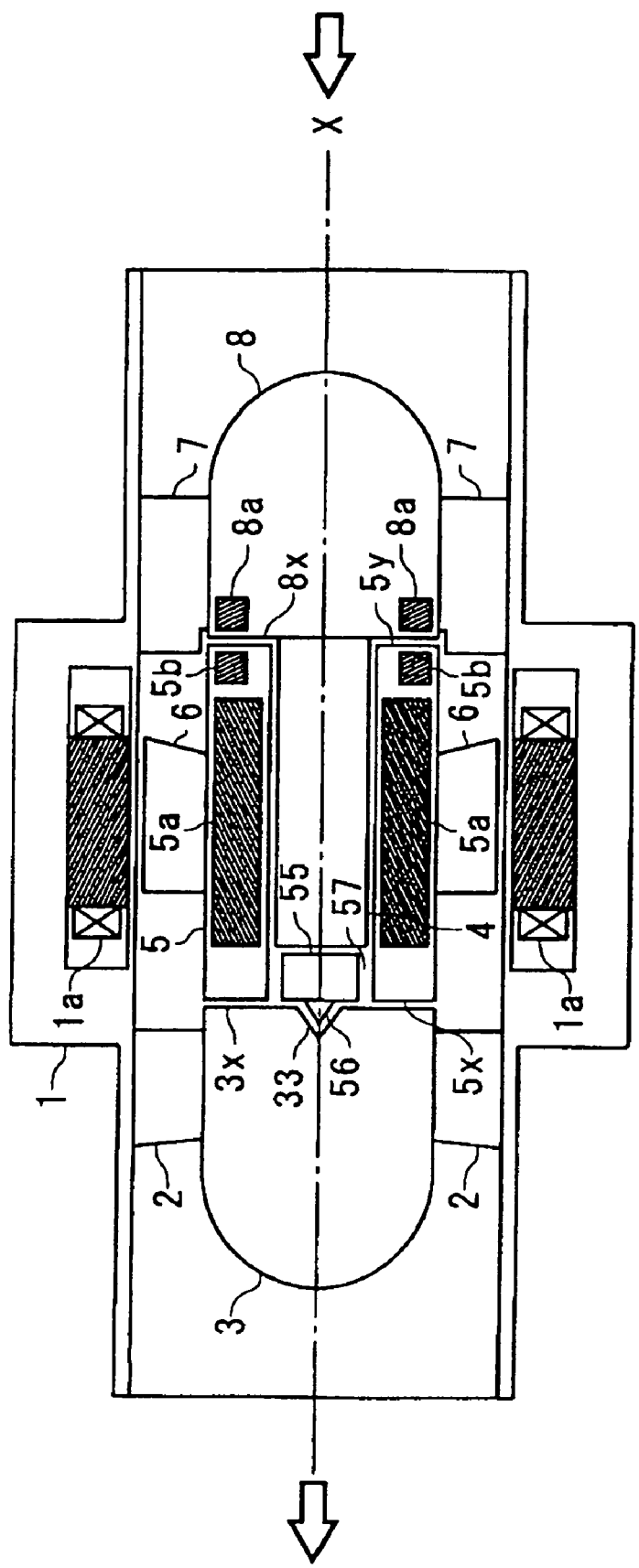
FIG. 16 is a cross-sectional view showing a configuration of an artificial heart pump in accordance with a ninth embodiment of the present invention.

Referring to the drawings, a ninth embodiment of the present invention will be described hereinafter. FIG. 16 is a cross-sectional view showing a configuration of an artificial heart pump in accordance with the present embodiment. In FIG. 16, same portions as in FIG. 1 will be provided with same symbols, and the detailed description thereof will be omitted.

Being different from the artificial heart pump in FIG. 1, the artificial heart pump shown in FIG. 16 has a configuration, in which the fixed shaft 4 is connected only to the fixed body 8; and the sleeve 5 is provided with the bottom portion 55 at the position to intervene between the fixed shaft 4 and the fixed body 3. Then, the protruding portion 56 in a shape of cone to have the top thereof on the rear side is provided to the center position of the rear end surface of the bottom portion 55 of the sleeve 5 that faces toward the front end surface 3x of the fixed body 3; and a groove 33 that is excavated so as to have a shape of a cone is provided to the center position of the front end surface 3x of the fixed body 3. The protruding portion 56 that is provided to the bottom portion 55 of the sleeve 5 and the groove 33 that is provided to the front end surface 3x of the fixed body 3 form a pivot bearing. Additionally, the vertex angle of the groove 33 is made to have an angle that is more than the vertex angle of the protruding portion 56.

Figure 17:
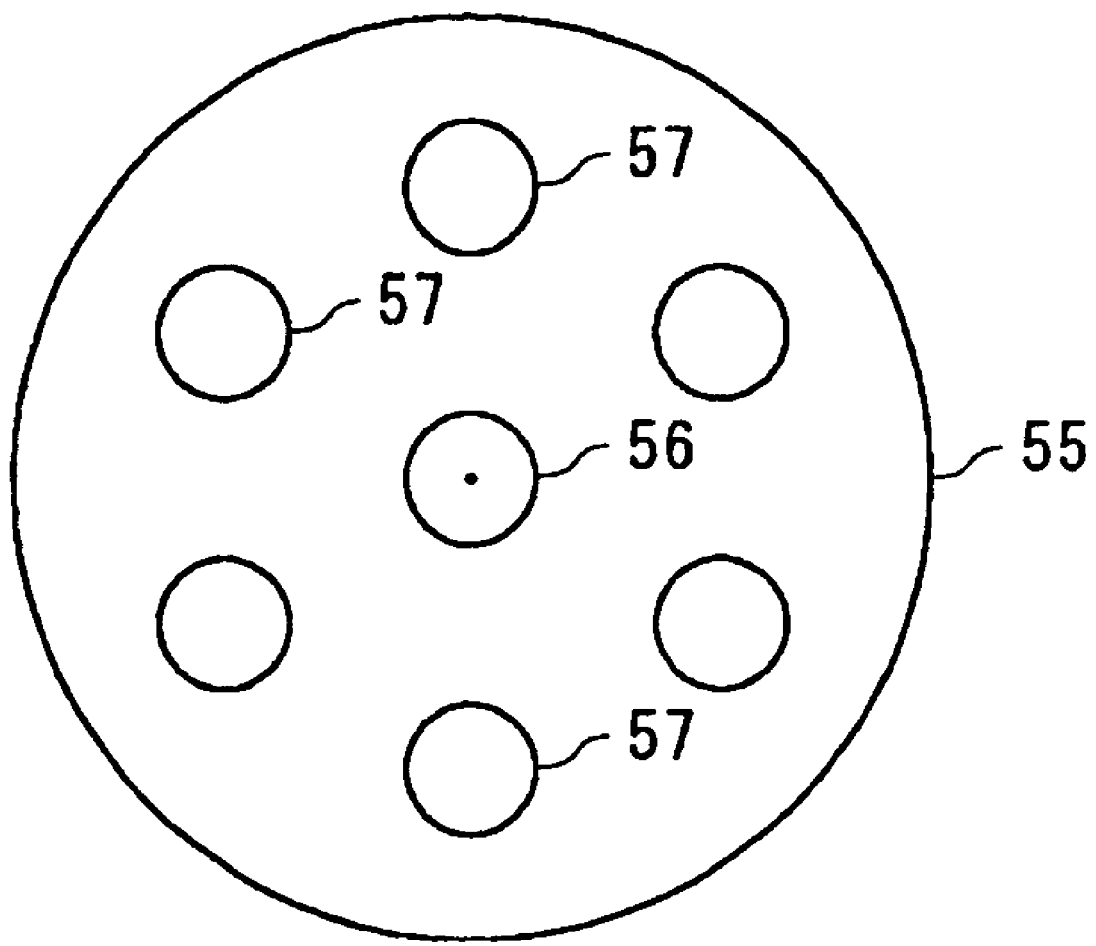
FIG. 17 is a diagram showing positional relations of through holes in an artificial heart pump in FIG. 16.

In addition, the bottom portion 55 of the sleeve 5 has a plurality of through holes 57 running through in an axial direction formed on the outer circumference of the protruding portion 56. As shown in FIG. 17, the through holes 57 are arranged so as to be equally spaced in a circumferential direction of the same radius, with the central axis X serving as a center. Then, by having a plurality of through holes 57 formed in the bottom portion 55 of the sleeve 5, the blood that flows into the gap being formed between the rear end surface 5x of the sleeve 5 and the front end surface 3x of the fixed body 3 can be shed through a gap between the inside wall surface of the sleeve 5 and the outside wall surface of the fixed shaft 4, and thereby, the blood can be prevented from stagnating.

Same as the first embodiment, when the artificial heart pump that is configured in such a manner as has been described hereinabove performs a normal rotating operation, hydro thrust loads are generated that serve as a force to shift the sleeve 5 forward by having the pressure on more rear side than the impeller vanes 6 increased. Then, by having the magnetic forces of repulsion by the permanent magnets 5b and 8a act so as to balance with the hydro thrust loads, it is possible to prevent the rear end surface 5x of the sleeve 5 from coming into contact with the front end surface 3x of the fixed body 3, and to prevent the front end surface 5y of the sleeve 5 from coming into contact with the rear end surface 8x of the fixed body 8.

In addition, since the hydro thrust load is small during start-ups, shutdowns, and the like, the sleeve 5 shifts backward by the magnetic forces of repulsion by the permanent magnets 5b and 8a. Therefore, the rear end surface 5x of the sleeve 5 and the front end surface 3x of the fixed body 3 try to come into contact with each other, and thereby, the top of the protruding portion 56 on the bottom portion 55 of the sleeve 5 comes into contact with the groove 33 that is provided to the front end surface 3x of the fixed body 3. By this, when the sleeve 5 shifts backward so as to come into contact with the fixed body 3 during a start-up and a shutdown, the contact occurs only at the top of the protruding portion 56, which can reduce the contact area. In consequence, a wear during the contact can be restrained, and at the same time, the hemolyzing performance can be prevented from deteriorating.

In addition, the present embodiment has been described based on the configuration of the first embodiment shown in FIG. 1. However, in the configurations shown in FIG. 3, FIG. 4A, and FIG. 5A, the fixed shaft 4 may be separated from the fixed body 3; a groove 33 may be provided to the front end surface 3x of the fixed body 3; and the sleeve 5 may include the bottom portion 55 that is provided with the protruding portion 56 and the through holes 57, in the similar manner. Moreover, in the configurations of the above-mentioned second and the seventh embodiments, the fixed shaft may be separated from the fixed body 3; the groove 33 may be provided to the front end surface of the fixed body 3; and the sleeve 5 may include the bottom portion 55 that is provided with the protruding portion 56 and the through holes 57 in the same manner.

Figure 18:
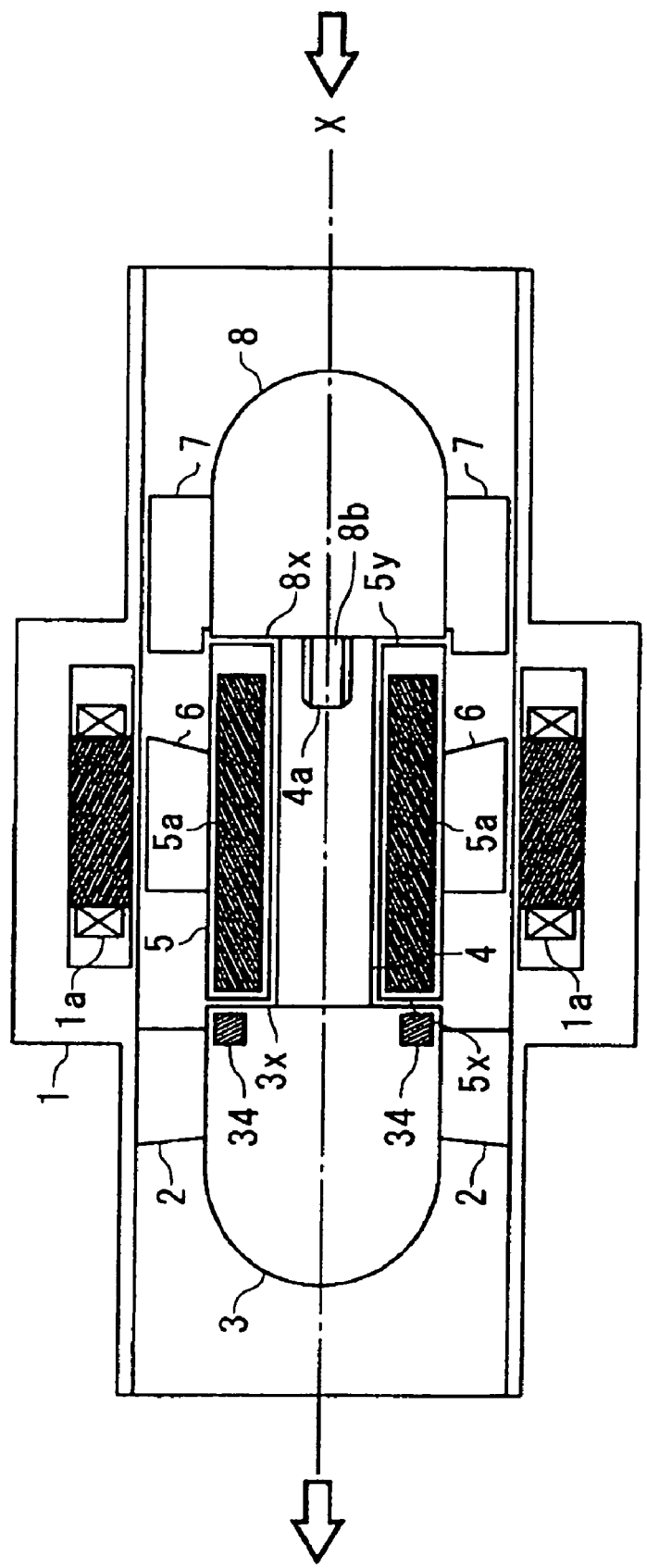
FIG. 18 is a cross-sectional view showing a configuration of an artificial heart pump having magnetic bearings consisting of magnetic bodies.

Additionally, in the above-mentioned first through the ninth embodiments, passive type of repulsive magnetic bearings are configured by the permanent magnets 5b and 8a that are housed in the sleeve 5 and the fixed body 8. However, as shown in FIG. 18, instead of providing the permanent magnets 5b and 8a, the fixed body 3 may house a ring-shaped magnetic body 34 on the side of the front end surface therein; and the front end surface of the magnetic body 34 may face toward the rear end surface of the polar anisotropic permanent magnet 5a. By being configured in such a manner as mentioned hereinabove, a force of gravity that is in the opposite direction to a thrust force of repulsion during rotation is generated between the magnetic body 34 and the polar anisotropic permanent magnet 5a, and thereby, magnetic bearings can be constructed by the magnetic body 34 and the polar anisotropic permanent magnet 5a. Moreover, FIG. 18 shows a configuration that includes magnetic bearings by the magnetic body 34 and the polar anisotropic permanent magnet 6a, in addition to the configuration of FIG. 1.

Tenth Embodiment

Figure 19:
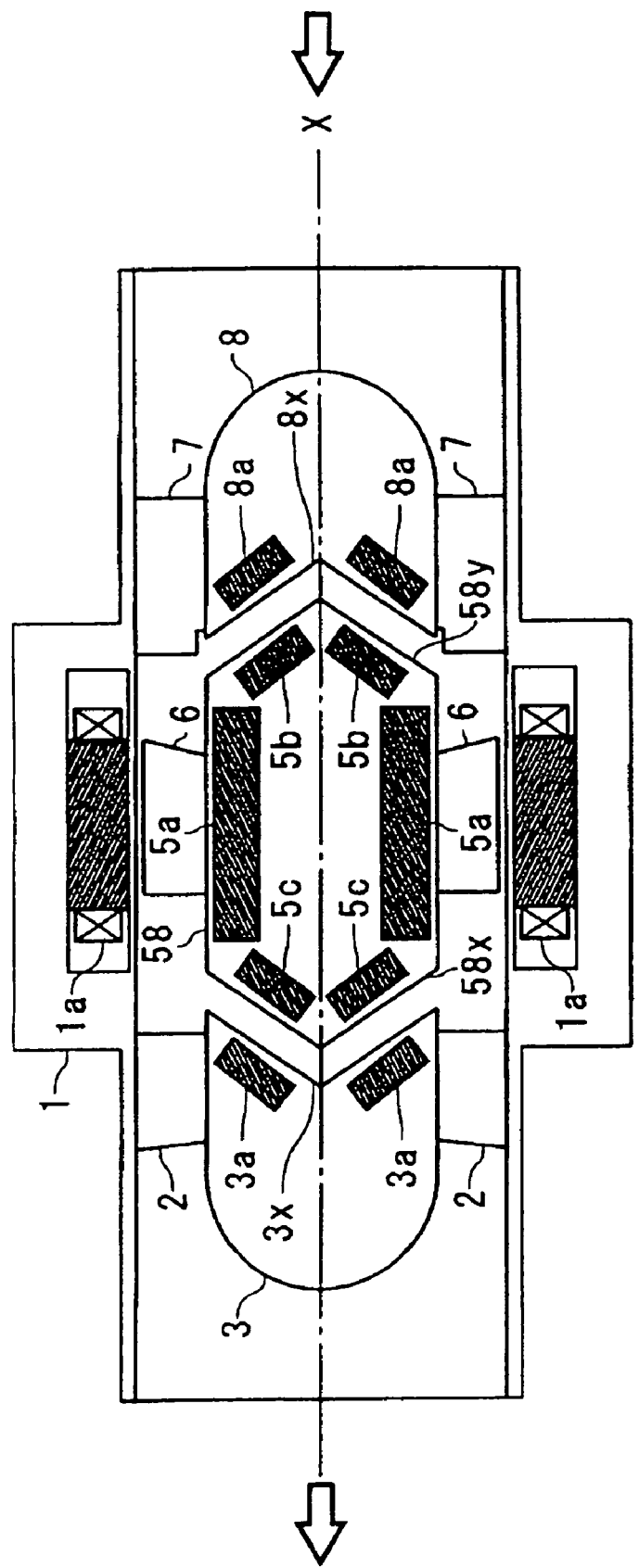
FIG. 19 is a cross-sectional view showing a configuration of an artificial heart pump in accordance with a tenth embodiment of the present invention.

Referring to the drawings, a tenth embodiment of the present invention will be described hereinafter. FIG. 19 is a cross-sectional view showing a configuration of an artificial heart pump in accordance with the present embodiment. In FIG. 19, same portions as in FIG. 1 will be provided with same symbols, and the detailed description thereof will be omitted.

Being different from the artificial heart pump in FIG. 1, the artificial heart pump in FIG. 19 is provided with the impeller 58 having both end surfaces in the X-shaft direction formed so as to have a conical convex surface, instead of the fixed shaft 4 and the sleeve 5; wherein, the front end surface 3x of the fixed body 3 is formed so as to have a conical concave surface in the same manner as the rear end surface 58x of the impeller 58, and the rear end surface 8x of the fixed body 8 is formed so as to have a conical concave surface in the same manner as the front end surface 58y of the impeller 58. In addition, each of the front end surface 3x of the fixed body 3 and the rear end surface 8x of the fixed body 8 has a plurality of spiral grooves for generation of thrust hydrodynamic pressure 100 (See FIG. 2.), formed thereon, respectively, that function so as to serve as the dynamic bearings. Furthermore, same as the fixed body 50 in FIG. 10, the impeller 58 has the impeller vanes 6 installed to the outside wall surface thereof so as to stick out, and houses the polar anisotropic permanent magnet 5a therein.

Then, each side of the front end surface and the rear end surface of the impeller 58 houses the permanent magnets 5b and 5c, respectively, that are shaped in a ring and tapered so as to be conical. The permanent magnet 5b has the front end surface thereof formed so as to be approximately in parallel with the front end surface of the impeller 58, and the permanent magnet 5c has the rear end surface thereof formed so as to be approximately in parallel with the rear end surface of the impeller 58. In addition, the fixed body 3 houses a permanent magnet 3a that includes the front end surface thereof being approximately in parallel with the rear end surface of the permanent magnet 5c and that is shaped in a ring and tapered so as to be conical; and the fixed body 8 houses a permanent magnet 8a that includes the rear end surface being approximately in parallel with the front end surface of the permanent magnet 5b and that is shaped in a ring and tapered so as to be conical.

Figure 20:
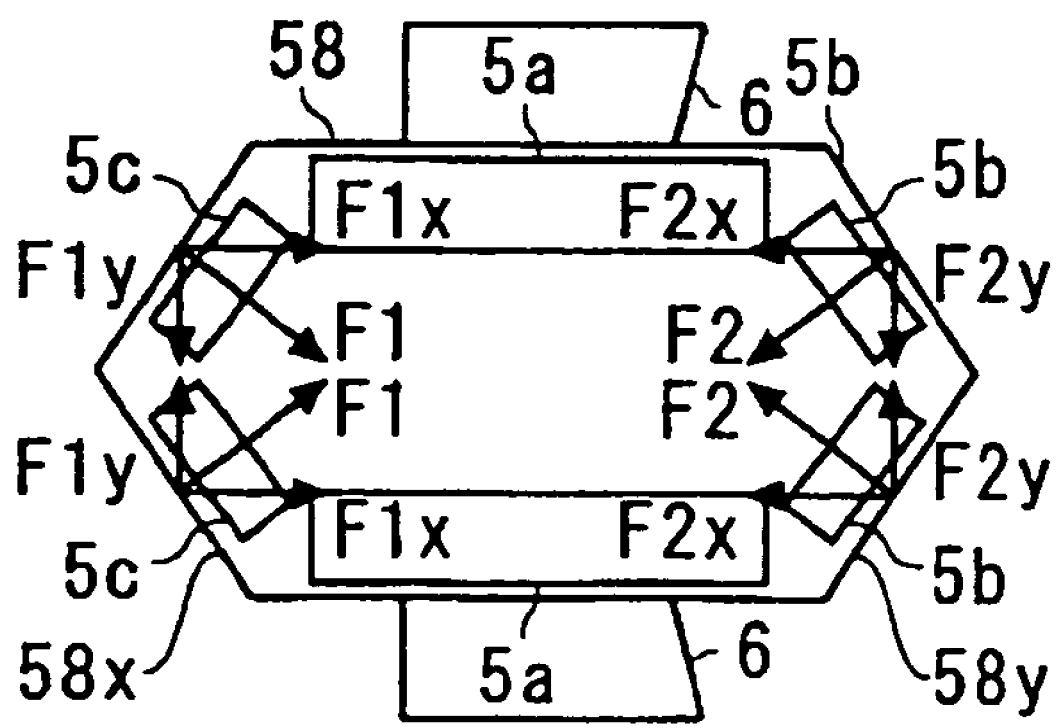
FIG. 20 is a diagram showing the relations of repulsive magnetic forces by permanent magnets in an artificial heart pump in FIG. 19.

In consequence, between the fixed body 3 and the impeller 58, magnetic forces of repulsion by the permanent magnets 3a and 5c act; and between the fixed body 8 and the impeller 58, magnetic forces of repulsion by the permanent magnets 8a and 5b act. Moreover, due to the hydrodynamic pressures by the dynamic bearings, the impeller 58 is supported in the axial and the radial directions without contact. To be specific, as shown in FIG. 20, in the impeller 58, the magnetic forces of repulsion F1 by the permanent magnets 3a and 5c and the magnetic forces of repulsion F2 by the permanent magnets 8a and 5b are applied to the rear end surface and the front end surface of the impeller 58, respectively, in an approximately vertical manner.

Since each of the magnetic forces of repulsion F1 and F2 is provided with angles in the direction of the X shaft and in the radial direction being vertical to the X shaft, respectively, the magnetic forces of repulsion F1 and F2 can be broken down into the forces in the direction of the X shaft F1x and F2x, and into the forces in the radial direction F1y and F2y. In consequence, since the radial forces F1y and F2y are applied to the rear end surface and the front end surface of the impeller 58 so as to surround them, respectively, the radial forces F1y and F2y act so as to serve as the journal bearings. In addition, since the forces F1x and F2x in the direction of the X shaft are applied as forces in the opposite direction, the forces F1x and F2x in the direction of the X shaft act so as to serve as the thrust bearings.

As described hereinabove, in accordance with the present embodiment, since the journal bearings and the thrust bearings can be constructed by the permanent magnets 3a, 8a, 5b, and 5c, the rotating shaft 4 is not necessary, while it is necessary in accordance with the first through the fourth embodiments. In consequence, the positions to install the polar anisotropic permanent magnet 5a and the permanent magnets 5b and 5c can be shifted toward the inside diameter side, so that the outside diameter of the impeller 50 of the artificial heart pump in accordance with the present embodiment can be made smaller than the outside diameter of the sleeves 5 of the artificial heart pumps in accordance with the other embodiments, whereby the radial configuration of the artificial heart pump can be downsized.

Figure 21:
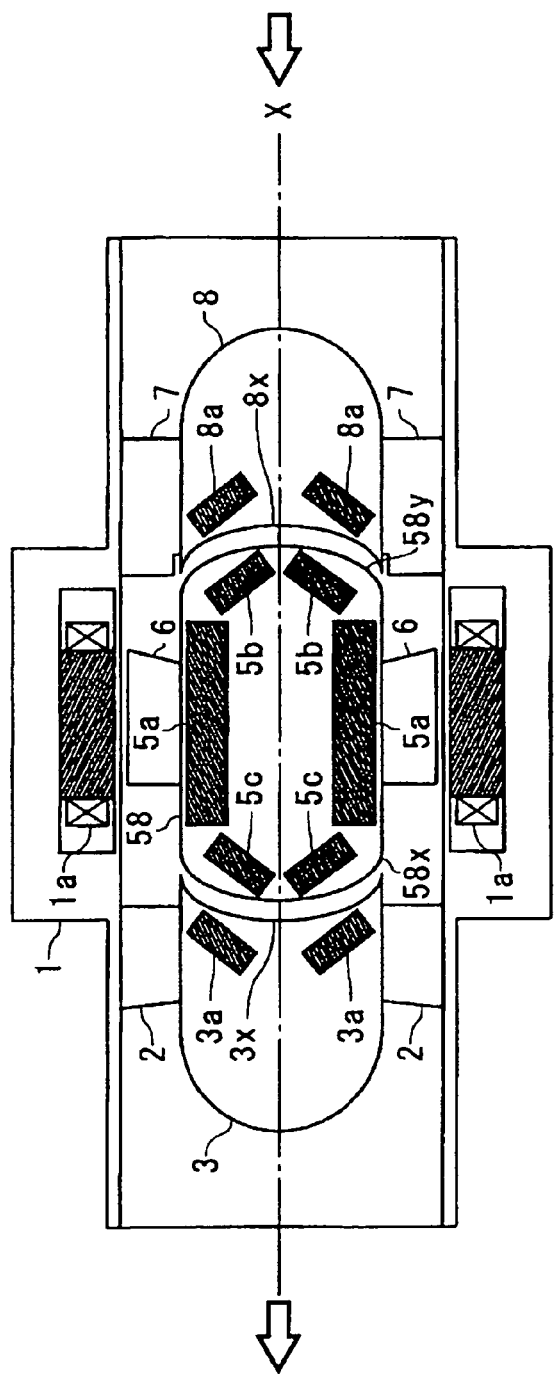
FIG. 21 is a cross-sectional view showing another configuration of an artificial heart pump in accordance with a tenth embodiment of the present invention.

In addition, in accordance with the present embodiment, both end surfaces 58x and 58y in the direction of the X shaft of the impeller 58 are formed so as to be conical. However, as shown in FIG. 21, both end surfaces 58x and 58y in the direction of the X shaft of the impeller 58 may be formed so as to be spherical, and at the same time, the front end surface 3x of the fixed body 3 and the rear end surface 8x of the fixed body 8 may be formed so as to be spherical, respectively. At this time, each of the front end surface of the permanent magnet 5b, the rear end surface of the permanent magnet 5c, the front end surface of the permanent magnet 3a, and the rear end surface of the permanent magnet 8a may be tapered so as to be conical, and may be formed so as to be spherical.

Moreover, same as the seventh embodiment, in accordance with the present embodiment, in a plurality of stages of impeller vanes may be installed to the impeller 8, and at the same time, stationary vanes sticking out from the housing 1 may be installed between the stages.

Eleventh Embodiment

By taking an artificial heart pump having the configuration in FIG. 1 as an example, an eleventh embodiment of the present invention will be described hereinafter.

Figure 22A:
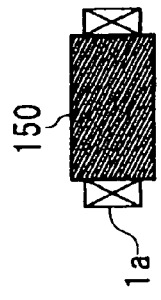
FIG. 22A is a schematic diagram showing a configuration of a stator coil that is equipped with a slot.
Figure 22B:
FIG. 22B is a schematic diagram showing a configuration of a stator coil having no slots.

In an artificial heart pump in accordance with the present embodiment, the motor stators 1a include stator coils having no slots, instead of including stator coils (stator coils that have slots), which have a plurality of slots, serving as a part of a core of a magnetic coil, arranged in the circumferential direction of the housing 1, and which have each slot wound around by a magnetic coil. In consequence, in case of a stator coil having a slot as shown in FIG. 22A, the size in the radial direction of the housing 1 is affected by the size of the slot 150. However, by including a stator coil that does not have a slot as shown in FIG. 22B, an effect of the size of the slot 150 can be eliminated, and as a result, the radial size of the housing 1 can be made smaller, whereby it is made possible to downsize the artificial heart pump.

In addition, the present embodiment has been described by taking the artificial heart pump, having the configuration shown in FIG. 1, as an example. However, the present embodiment is not limited to the artificial heart pump having the configuration in FIG. 1, but the configuration of the present embodiment may be applicable to the artificial heart pumps in accordance with the first through the tenth embodiments, or to an artificial heart pump having a conventional configuration, by having the motor stators 1a consist of stator coils that have no slots.

Twelfth Embodiment

Figure 23:
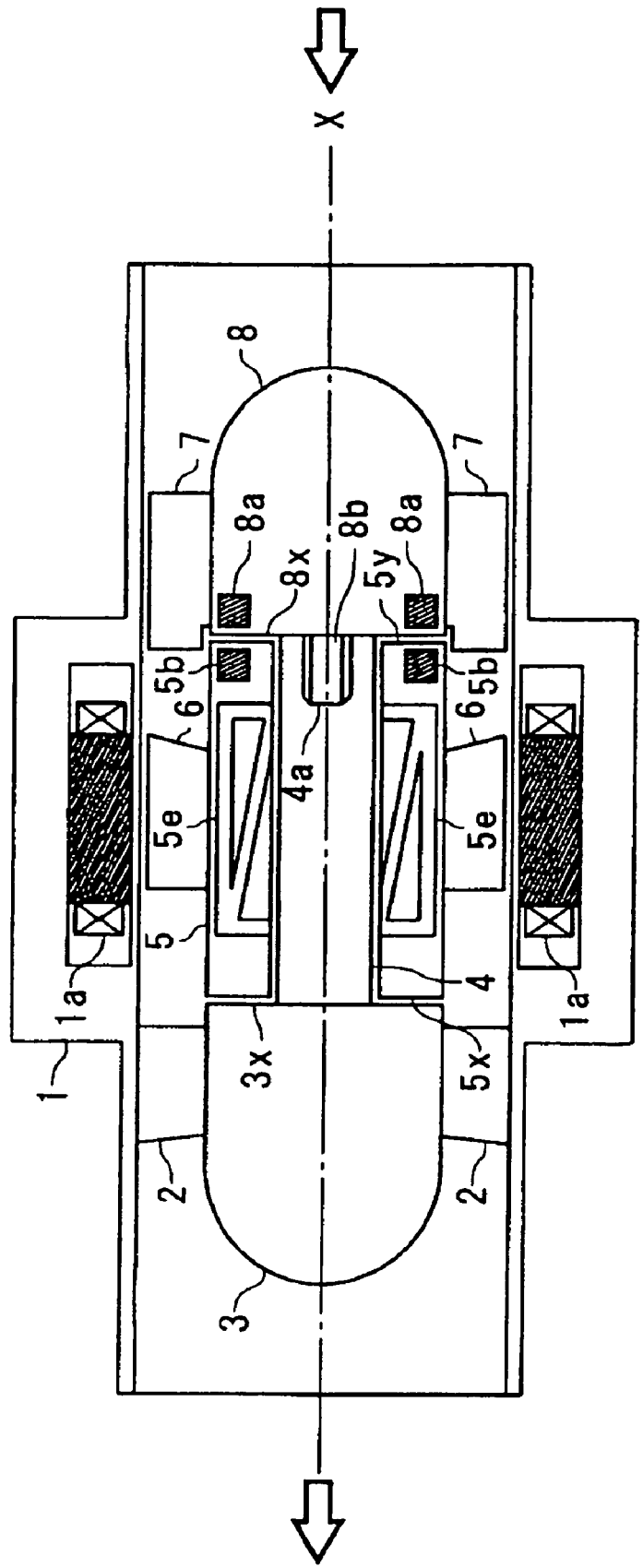
FIG. 23 is a cross-sectional view showing another configuration of an artificial heart pump in accordance with a twelfth embodiment of the present invention.
Figure 24:
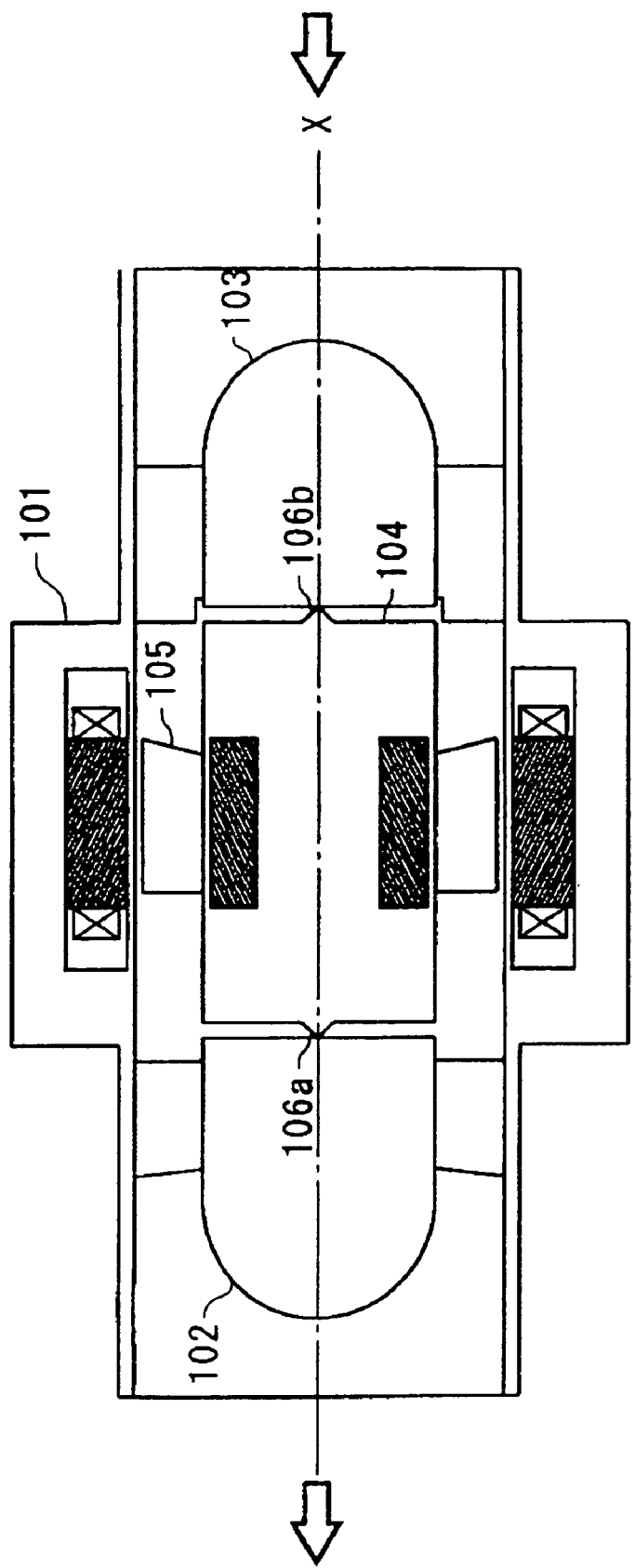
FIG. 24 is a cross-sectional view showing a configuration of a conventional artificial heart pump employing pivot bearings.
Figure 25:
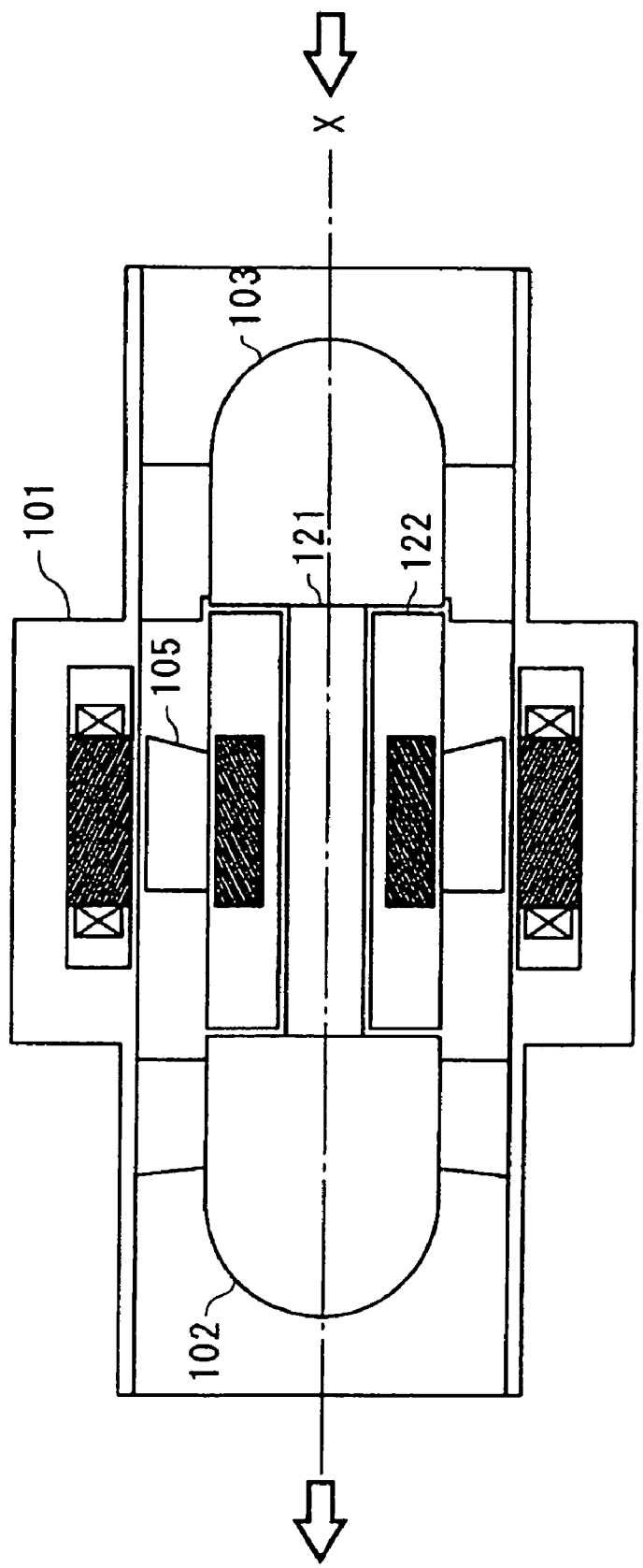
FIG. 25 is a cross-sectional view showing a configuration of a conventional artificial heart pump employing hydrodynamic bearings.

Referring to the drawings, a twelfth embodiment of the present invention will be described hereinafter. FIG. 23 is a cross-sectional view showing a configuration of an artificial heart pump in accordance with the present embodiment. In FIG. 23, same portions as in FIG. 1 will be provided with same symbols, and the detailed description thereof will be omitted.

Being different from the artificial heart pump in FIG. 1, the artificial heart pump shown in FIG. 23 has the inside of the sleeve 5 provided with a cylindrical cage-shaped rotor 5e, in which induced electric currents flow, based on the rotating magnetic fields being generated by the motor stators 1a, instead of the polar anisotropic permanent magnet 5a. To be specific, the artificial heart pump in accordance with the present embodiment does not have a synchronous motor consist of the motor stators 1a and the polar anisotropic permanent magnet 5a in such a manner as the artificial heart pumps in accordance with the other embodiments, but has an induction motor consist of the motor stators 1a and the cage-shaped rotor 5e. As a result, being different from a case in which the sleeve 5 is rotated by a power being generated by the synchronous motor as in accordance with the other embodiments, the sleeve 5 is rotated by the power being generated by the induction motor, so that a loss of synchronism that occurs when the load fluctuates can be restrained.

In addition, the present embodiment has been described by taking the artificial heart pump having the configuration in FIG. 1 as an example. However, the artificial heart pump is not limited to the present embodiment, and the configuration of the present embodiment may be applicable to each configuration of the first through the eleventh embodiments, or to the conventional configuration, by employing the cage-type rotor 5e in place of the polar anisotropic permanent magnet 5a.

Moreover, in the artificial heart pump being configured in accordance with each of the above-mentioned embodiments, the hardness of the materials that compose the rotating members, such as the sleeve 5 and the impeller vanes 50, 55, and 58 that are rotary driven, may be different from the hardness of the materials that compose the fixed members, such as the fixed bodies 3 and 8 and the fixed shafts 4, 41 and 42 that are fixed to the housing 1. To be specific, for example, titanium alloy that is carbonitrided may be employed as the materials that compose the rotating members, and unprocessed titanium alloy may be employed as the materials that compose the fixed members. On the contrary, the unprocessed titanium alloy may be employed as the materials that compose the rotating members, and the carbonitrided titanium alloy may be employed as the materials that compose the fixed members. In addition, carbonitriding means a process to heat an object so as to be carburized in a gas atmosphere in which ammonia (NH3) is added to the metamorphosed gas having carburizing property, such as natural gas, city gas, propane, butane, and the like, or added to the gas having carburizing property that is generated by putting drops of liquid.

Since the fixing members and the rotating members are composed of materials that are different in hardness in such a manner as described hereinabove, a seizure during contact can be prevented from occurring, and thereby, the sliding property thereof can be maintained as favorable. In addition, by employing titanium alloy for a material that is to be used for each portion, not only the biocompatibility thereof can be compensated, but also the temperature of the atmosphere during treatment can be lowered by applying the carbonitriding process to the treatment so as to produce titanium alloys having different hardness, and thereby thermal deformation of a member to be treated can be restrained.

What is claimed is:

1. An artificial heart pump comprising:
a housing having an inlet and an outlet for a blood flow;
a fixed shaft that is fixed to a center position inside the housing in a direction from the inlet to the outlet;
a first fixed body, which is fixed inside the housing with a plurality of stationary vanes at an inlet side of the housing and connected to a front-end of the fixed shaft;
a second fixed body, which is fixed inside the housing with a plurality of diffuser vanes at an outlet side of the housing and connected to a rear-end of the fixed shaft;
a rotating body that is engaged to the fixed shaft and rotatably supported by a circumferential surface of the fixed shaft;
a plurality of impeller vanes that stick out from an outside wall surface of the rotating body;
motor stators, which are placed in the housing, located at positions encircling the rotating body, and generate a rotating magnetic field therein;
a first and a second permanent magnet, which are housed inside the rotating body and the first fixed body, respectively, generating a repulsing magnetic force working in an opposite direction to thrust loads that are applied from a rear side toward a front side in an axial direction of the impeller vanes when the rotating body rotates; and
a plurality of protruding portions, which encircles the fixed shaft on either a front-end surface of the second fixed body facing to a rear-end surface of the rotating body or the rear-end surface of the rotating body facing to the front-end surface of the second fixed body;
wherein, the first and the second fixed bodies are provided with structures that enable separation from the fixed shaft;
only one at a time of the first and the second fixed bodies can be separated from the other fixed bodies using the structures that enable separation; and
the blood flow is in an axial direction of the fixed shaft, by having the rotating body rotate by the rotating magnetic field of the motor stators during operation.

2. The artificial pump as described in claim 1:
wherein, the structures that enable separation include:
a protruding portion that is provided to a contact surface of the first fixed body with the fixed shaft, and that is inserted into the fixed shaft; and
a hole that is provided to a contact surface of the fixed shaft with the first fixed body, and into which the protruding portion of the first fixed body is inserted.

3. The artificial heart pump as described in claim 2:
wherein, the second fixed body is fixed to the housing; and
the fixed shaft is connected to the second fixed body so as to be fixed.

4. The artificial heart pump as described in claim 2:
wherein, the first fixed body is provided with the plurality of stationary vanes that stick out from an outside wall surface thereof toward an inside wall surface of the housing; and
wherein, the stationary vanes have inner edges thereof connected to the first fixed body, and have outer edges thereof separated from the housing.

5. The artificial heart pump as described in claim 2:
wherein, the first fixed body is provided with the plurality of stationary vanes that stick out from an outside surface thereof toward an inside wall surface of the housing; and
wherein, the stationary vanes have inner edges thereof separated from the first fixed body, and have outer edges thereof connected to the housing.

6. The artificial heart pump as described in claim 2 includes:
an adjustment ring that is installed around the protruding portion, and adjusts a distance between the first and the second fixed bodies.

7. The artificial heart pump as described in claim 2:
wherein, the first fixed body is installed to a front side of the rotating body in an axial direction thereof; and
the second fixed body is installed to a rear side of the rotating body in the axial direction thereof.

8. The artificial heart pump as described in claim 2:
wherein, the first fixed body is installed to a rear side of the rotating body in an axial direction thereof; and
the second fixed body is installed to a front side of the rotating body in the axial direction thereof.

9. The artificial heart pump as described in claim 1:
wherein, the structures that enable separation include:
a protruding portion that is provided to a contact surface of the fixed shaft with the first fixed body, and that is inserted into the first fixed body; and
a hole that is provided to a contact surface of the first fixed body with the fixed shaft, and into which the protruding portion of the fixed shaft is inserted.

10. The artificial heart pump as described in claim 9:
wherein, the second fixed body is fixed to the housing; and
the fixed shaft is connected to the second fixed body so as to be fixed.

11. The artificial heart pump as described in claim 9:
wherein, the first fixed body is provided with the plurality of stationary vanes that stick out from an outside wall surface thereof toward an inside wall surface of the housing; and
wherein, the stationary vanes have inner edges thereof connected to the first fixed body, and have outer edges thereof separated from the housing.

12. The artificial heart pump as described in claim 9:
wherein the first fixed body is provided with a plurality of stationary vanes that stick out from an outside wall surface thereof toward an inside wall surface of the housing; and wherein, the stationary vanes have inner edges thereof separated from the first fixed body, and have outer edges thereof connected to the housing.

13. The artificial heart pump as described in claim 9 includes:
an adjustment ring that is installed around the protruding portion, and adjusts a distance between the first and the second fixed bodies.

14. The artificial heart pump as described in claim 9:
wherein, the first fixed body is installed to a front side of the rotating body in an axial direction thereof; and
the second fixed body is installed to a rear side of the rotating body in the axial direction thereof.

15. The artificial heart pump as described in claim 9:
wherein, the first fixed body is installed to a rear side of the rotating body in an axial direction thereof and
the second fixed body is installed to a front side of the rotating body in the axial direction thereof.

16. The artificial heart pump as described in claim 1
wherein, the structures that enable separation include a first and a second fixed shaft that are separated from the fixed shaft;
wherein, the first fixed shaft is connected to the first fixed body, and at the same time, the second fixed shaft is connected to the second fixed body; and
wherein, the first and the second fixed shafts are fixed by having the first and the second fixed bodies fastened to the housing.

17. The artificial heart pump as described in claim 16:
wherein, the first and the second fixed bodies are provided with the plurality of stationary vanes and diffuser vanes, respectively, that have inner edges thereof connected to an outside wall surface of the first and the second fixed bodies, and that stick out toward an inside wall surface of the housing; and
wherein, by having outer edges of the stationary and diffuser vanes connected to the housing, the first and the second fixed bodies are fixed to the housing.

18. The artificial heart pump as described in claim 16:
wherein, the first fixed body is installed to a front side of the rotating body in an axial direction thereof; and
the second fixed body is installed to a rear side of the rotating body in the axial direction thereof.

19. The artificial heart pump as described in claim 16:
wherein, the first fixed body is installed to a rear side of the rotating body in an axial direction thereof; and
the second fixed body is installed to a front side of the rotating body in the axial direction thereof.

20. An artificial heart pump comprising:
a housing having an inlet and an outlet for a blood flow;
a fixed shaft that is fixed to a center position inside the housing in a direction from the inlet to the outlet;
a first fixed body that is fixed inside the housing with a plurality of stationary vanes at an inlet side of the blood flow and free from a physical connection with the fixed shaft;
a second fixed body, which is fixed inside the housing with a plurality of diffuser vanes at an outlet side of the blood flow and connected to a rear end of the fixed shaft;
a rotating body which is substantially cup shaped, is installed between the first and the second fixed bodies, engaged to the fixed shaft, and rotatably supported by a circumferential surface of the fixed shaft, a front-end surface of the fixed shaft, and a rear-end surface of the first fixed body;
a plurality of impeller vanes that stick out from an outside wall surface of the first rotating body; and
motor stators that are placed in the housing, located at positions encircling the rotating body, and generate a rotating magnetic field therein;
wherein, the rotating body covers the circumferential surface of the fixed shaft and the front-end surface of the fixed shaft;
a bottom portion is formed in a front-end surface of the rotating body;
at least a part of the bottom portion is inserted into a space between the rear-end surface of the first fixed body and the front-end surface of the fixed shaft;
the bottom portion of the rotating body is supported by the rear-end surface of the first fixed body without physical contact;
a hole allowing blood flow is formed at a center position of the bottom portion of the rotating body;
the rotating body and the first fixed body have insides thereof provided with a first and a second permanent magnets, respectively, which generating a repulsing magnetic force working in an opposite direction to thrust loads, which are applied from a rear side toward a front side in an axial direction of the impeller vanes, when the rotating body rotates; and
blood flow is in an axial direction of the fixed shaft, by having the rotating body rotate by the rotating magnetic field of the motor stators during operation.

21. The artificial heart pump as described in claim 20:
wherein, the rotating body is provided with through holes that penetrate through the bottom portion in an axial direction.

22. The artificial heart pump as described in claim 1 further comprising:
a plurality of stationary vanes that are fixed to an inside wall surface of the housing, and at the same time, stick out from an inside wall surface of the housing toward an outside wall surface of the rotating body;
wherein, the rotating body has the impeller vanes installed to form a plurality of stages in the axial direction; and has the stationary vanes installed between the impeller vanes of the plurality of stages that are adjacent to each other in the axial direction.

23. The artificial heart pump as described in claim 1:
wherein, the motor stators include a stator coil that is provided with no slots.

24. The artificial heart pump as described in claim 1:
wherein, the motor stators include a stator coil that is provided with a slot.

25. The artificial heart pump as described in claim 1 further comprising:
an anisotropic permanent magnet, which is placed in the rotating body and generates a magnetic field perpendicular to an outside wall surface of the rotating body.

26. The artificial heart pump as described in claim 1 further comprising:
a rotor, which is placed in the rotating body, and rotates the rotating body with a force produced by induced electric currents generated by being placed within the rotating magnetic field of the motor stators.

27. The artificial heart pump as described in claim 1:
wherein, hydrodynamic bearings are provided between contact surfaces of the fixed bodies and the rotating body.

28. The artificial heart pump as described in claim 1:
wherein the fixed bodies and the rotating body comprise materials having different hardnesses.

* * * * *